US010934575B2

(12) United States Patent
Grosveld et al.

(10) Patent No.: US 10,934,575 B2
(45) Date of Patent: Mar. 2, 2021

(54) METHOD FOR ANALYSING THE INTERACTION OF NUCLEOTIDE SEQUENCES IN A THREE-DIMENSIONAL DNA STRUCTURE

(71) Applicant: Erasmus Universiteit Medisch Centrum Rotterdam, Rotterdam (NL)

(72) Inventors: Frank Grosveld, Rotterdam (NL); Tobias Knoch, Rotterdam (NL)

(73) Assignee: Erasmus Universiteit Medisch Centrum Rotterdam, Rotterdam (NL)

( * ) Notice: Subject to any disclaimer, the term of this patent is extended or adjusted under 35 U.S.C. 154(b) by 249 days.

(21) Appl. No.: 15/037,210

(22) PCT Filed: Nov. 18, 2014

(86) PCT No.: PCT/IB2014/002485
§ 371 (c)(1),
(2) Date: May 17, 2016

(87) PCT Pub. No.: WO2015/071748
PCT Pub. Date: May 21, 2015

(65) Prior Publication Data
US 2016/0289738 A1 Oct. 6, 2016

(30) Foreign Application Priority Data
Nov. 18, 2013 (GB) .................................. 1320351.8

(51) Int. Cl.
*C12Q 1/68* (2018.01)
*C12Q 1/6806* (2018.01)
*C12Q 1/682* (2018.01)
(52) U.S. Cl.
CPC ........... *C12Q 1/6806* (2013.01); *C12Q 1/682* (2013.01)

(58) Field of Classification Search
USPC ......... 435/6.1, 6.11, 6.12, 91.1, 91.2, 91.51; 436/94, 501; 536/23.1, 24.3, 24.33, 25.3
See application file for complete search history.

(56) References Cited

U.S. PATENT DOCUMENTS 7,348,178 B1 * 3/2008 Schneider ................ C12N 7/00
435/320.1
2010/0075861 A1 * 3/2010 De Laat ............... C12Q 1/6809
506/9

FOREIGN PATENT DOCUMENTS

WO  WO-2007/004057 A2  1/2007
WO  WO-2008/084405 A2  7/2008
(Continued)

OTHER PUBLICATIONS

Naumova et al., Analysis of long-range chromatin interactions using Chromosome Conformation Capture. Methods, 58, 192-203, 2012.*
(Continued)

*Primary Examiner* — Frank W Lu
(74) *Attorney, Agent, or Firm* — Marshall, Gerstein & Borun LLP

(57) ABSTRACT

The present invention provides a method for analysing the interaction of one or more nucleotide sequence(s) from one or more region(s) of interest with other nucleotides sequences in a three-dimensional DNA structure, comprising the steps of: (a) providing a sample of crosslinked DNA; (b) digesting the cross-linked DNA with a first restriction enzyme; (c) ligating the cross-linked nucleotide sequences; (d) reversing the cross-linking; e) fragmenting the ligation and ligated molecules from (d); (f) hybridising the fragments from (e) to one or more oligonucleotides representing the sequences which are adjacent to the cleavage site of the first restriction enzyme in order to enrich for the ends of the nucleotide sequences that have been ligated to another nucleotide sequence in step (c); and (g) analysing the (Continued)

nucleotide sequence of the enriched fragments in order to identify the nucleotide sequences involved in interaction(s).

10 Claims, 9 Drawing Sheets
(9 of 9 Drawing Sheet(s) Filed in Color)
Specification includes a Sequence Listing.

(56) References Cited

FOREIGN PATENT DOCUMENTS

| | | |
|---|---|---|
| WO | WO-2012005595 A2 | 1/2012 |
| WO | WO-2014/168575 A1 | 10/2014 |

OTHER PUBLICATIONS

Dixon et al., Topological domains in mammalian genomes identified by analysis of chromatin interactions, Nature, 485(7398):376-80 (2012).
Dostie et al., Chromosome Conformation Capture Carbon Copy (5C): a massively parallel solution for mapping interactions between genomic elements, Genome Res., 16(10):1299-309 (2006).
Ferraiuolo et al., From cells to chromatin: capturing snapshots of genome organization with 5C technology, Methods, 58(3):255-67 (2012).
International Search Report and Written Opinion, International Application No. PCT/IB2014/002485, dated Mar. 31, 2015.
Lieberman-Aiden et al., Comprehensive mapping of long-range interactions reveals folding principles of the human genome, Science, 326(5950):289-93 (2009).
Simonis et al., Nuclear organization of active and inactive chromatin domains uncovered by chromosome conformation capture-on-chip (4C), Nat. Genet., 38(11):1348-54 (2006).
Stadhouders et al., Multiplexed chromosome conformation capture sequencing for rapid genome-scale high-resolution detection of long-range chromatin interactions, Nat. Protoc., 8(3):509-24 (2013).
International Preliminary Report on Patentability, International Application No. PCT/IB2014/002485, dated May 24, 2016.
Dekker et al., Capturing Chromosome Conformation, Science, 295:1306-10 (2002).
Belmont et al., Visualization of G1 Chromosomes: A Folded, Twisted, Supercoiled Chromonema Model of Interphase Chromatid Structure, J. Cell Biol., 1994, vol. 127, No. 2, pp. 287-302.
Comings, Mechanisms of chromosome banding and implications for chromosome structure, Ann. Rev. Genet., 1978, 12, pp. 25-46.
Comings, The rationale for an ordered arrangement of chromatin in the interphase nucleus, American Journal of Human Genetics, 1968, 20(5) pp. 440-460.
Cremer et al., An ultraviolet Laser microbeam for 257 nm, Microscopica Acta, 1974, vol. 75, No. 4 pp. 331-337.
Cremer et al., Chromosome territories, nuclear architecture and gene regulation in mammalian cells, Nature Review Genetics, 2001, vol. 2, pp. 292-301.
Cremer et al., Detection of chromosome aberrations in metaphase and interphase tumor cells by in situ hybridization using chromosme-specific library probes, Human Genetics, 1988, 80, pp. 235-246.
Cremer et al., Rabl's Model of the Interphase Chromosome Arrangement Tested in Chines Hamster Cells by Premature Chromosome Condensation and Laser-UV-Microbeam Experiments, Human Genetics, 1982, vol. 60, pp. 46-56.
Finch et al., Solenoidal model for superstructure in chromatin, Proc Natl Acad Sci USA, 1976, vol. 73 No. 6 pp. 1897-1901.
Knoch et al., New three-dimensional organization of chromosome territories and the human cell nucleus: about the structure of a self replicating nano fabrication site, TAK Foresight, 1998, 9415. Paper presented at the Sixth Foresight Conference on Molecular Nanotechnology.
Knoch, Towards a holistic understanding of the human genome by determination and integration of Its sequential and three-dimensional organization, High Performance Computing in Science and Engineering, 2003, Springer-Verlag, pp. 421-440.
Kolovos et al., Targeted Chromatin Capture (T2C): a novel high resolution high throughput method to detect genomic interactions and regulatory elements, Epigentics & Chromatin, 2014, 7:10.
Kornberg et al., The Nucleosome, Sci Am 1981 244(2) pp. 48-60.
Lichter et al., Delineation of individual human chromosomes in metaphase and interphase cells by insitu suppression hybridzation using recombinant DNA libraries, Human Genetics, 1988, 80, pp. 224-234.
Luger et al Crystal structure of the nucleosome core particle at 2.8A resolution, Nature, 1997, vol. 389, pp. 251-260.
Olins et al., Spheroid Chromatin Units (v Bodies), Science, 1974, vol. 183, No. 4122, pp. 330-332.
Paulson et al., The Structure of Histone-depleted Metaphase Chromosomes, Cell, 1977, vol. 12, pp. 817-828.
Pienta et al., A Structural Analysis of the Role of the Nuclear Matrix and DNA Loops in the Organization of the Nucleus and Chromosome, Journal of Cell Science Supplement 1, 1984, pp. 123-135.
Roche, NimbleGen arrays user's guide, Sequence Capture Array Delivery version 3.2, 2015 www.nimblegen.com/seqcapez.
Sachs et al., A random-walk/giant-loop model for interphase chromosomes, Proc Natl Acad Sci USA, 1995, vol. 92, pp. 2710-2714.
Soler et al., The genome-wide dunamics of the binding of Ldb1 complexes during erythroid differentiation, Genes & Development, 2010, 24(3):277-289.
Splinter et al., 3C Technology: Analyzing the spatial organization of genomic loci In Vivo, Methods Enzymol., 2004, 375, pp. 493-507.
Tobias et al., On the detailed 3D multi-loop aggregate/rosette chromatin architecture and functional dynamic organization of the human and mouse genome, Abstract, Jun. 3, 2013.
Vogel et al., The internal order of the interphase nucleus, Humangenetik, 1974, 25(4) pp. 265-297.
Watson et al., Molecular structure of nucleic acids, A structure for deoxyribose nucleic acid, Nature, 1953, No. 4356 pp. 737-738.
Yokota et al., Regional differences in the compaction of chromatin in human G0/G1 interphase nuclei, Chromosome Research, 1997, 5, pp. 157-166.
Yokota, Evidence for the organization of chromatin in megabase pair-sized loops arranged along a random walk path in the human G0/G1 interhase nucleus, J. Cell Biol., Sep. 1995, vol. 130, No. 6, pp. 1239-1249.
Zuin et al., Cohesin and CTCF differentially affect chromatin architecture and gene expression in human cells, Proc Nat Acad Science, 2013, vol. 111 No. 3 pp. 996-1001.
Japanese Patent Application No. 2016-553748. Search Report. dated Jul. 23, 2018.
Knoch et al., The detailed 3D multi-loop aggregate/rosette chromatin architecture and functional dynamic organization of the human and mouse genomes, Epigenetics & Chromatin, 9:58 (2016).
Knoch, Approaching the Three-Dimensional Organization and Dynamics of the Human Genome, ICT for Bio-Medical Sciences, 2006, European Commission, DG Information Society & Media and DG Research, Brussels, Belgium (Jun. 30, 2006).
Thongjuea et al., r3Cseq: an R/Bioconductor package for the discovery of long-range genomic interactions from chromosome conformation capture and next-generation sequencing data, Nucleic Acids Res., 41(13):e132 (Jul. 2013).
Chen et al., Simultaneous detection of multiple transgenic components by multiplex PCR, Inspection and Quarantine Science, Modern Commodity Inspection Science and Technique, Issue 3 (2002).
Sun et al., High throughput analysis of differential expressed gene and its clinic impact, Chinese J. Cancer, 21(5):571-5 (2002).
Chinese Patent Application No. 201480062775.X, Search Report, dated Feb. 20, 2019.

* cited by examiner

FIG. 9A
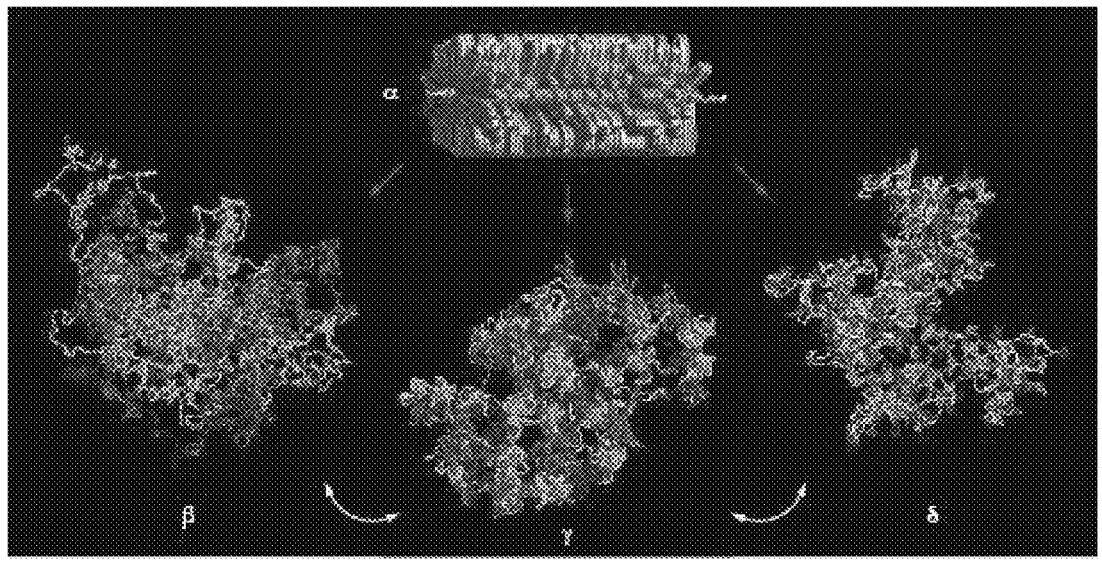
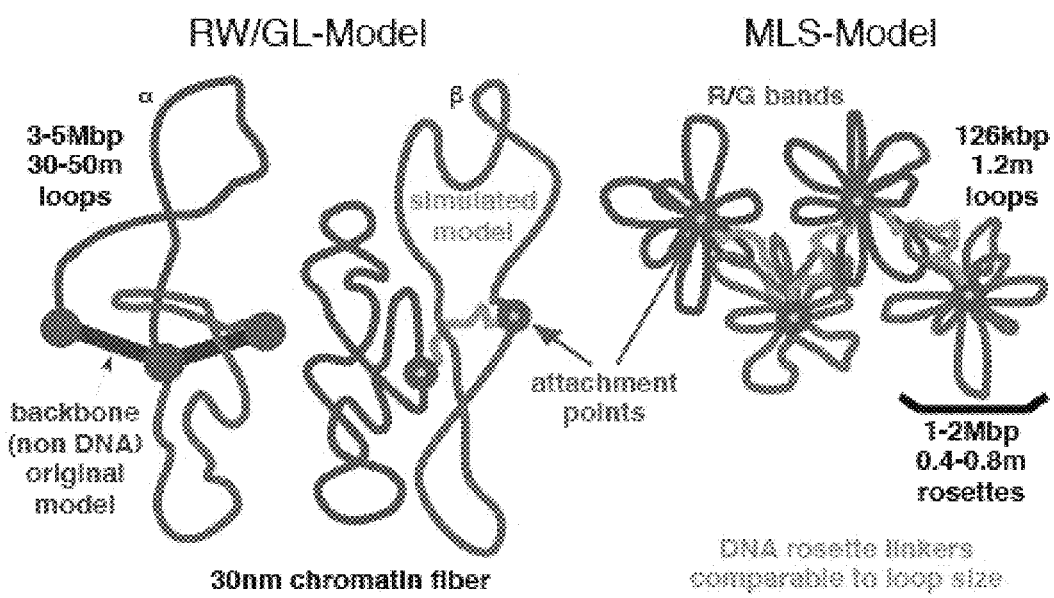
FIG. 9B

SEQUENCE LISTING

<160> NUMBER OF SEQ ID NOS: 2

<210> SEQ ID NO 1
<211> LENGTH: 19
<212> TYPE: RNA
<213> ORGANISM: Artificial Sequence
<220> FEATURE:
<223> OTHER INFORMATION: 3'UTR-directed siRNA, Scc1-1

<400> SEQUENCE: 1
acucagacuu caguguaua                                              19

<210> SEQ ID NO 2
<211> LENGTH: 19
<212> TYPE: RNA
<213> ORGANISM: Artificial Sequence
<220> FEATURE:
<223> OTHER INFORMATION: 3'UTR-directed siRNA, Scc1-2

<400> SEQUENCE: 2
aggacagacu gaugggaaa                                              19

METHOD FOR ANALYSING THE INTERACTION OF NUCLEOTIDE SEQUENCES IN A THREE-DIMENSIONAL DNA STRUCTURE

FIELD OF THE INVENTION

The present invention relates to a method for analysing the interaction of nucleotide sequences in a three-dimensional DNA structure such as chromatin.

BACKGROUND TO THE INVENTION

A number of recent studies have shown that the genome is organised in a number of self-associating domains that are separated by linker regions. These so-called "topological domains", generally range from 300 kilobasepairs (kb) to 1 megabasepair (1 Mb). A topological domain consists of a series of chromatin loops, where a loop is defined as bringing two parts of the chromatin in close proximity allowing interaction between the regions, although the latter need not be the case. These loops are dynamic and dependent on a large number of proteins including CTCF and cohesion and a series of transcription factors required for the regulation of genes within the domain. A number of loops within a domain are thought to be purely structural, i.e to enable folding of the genome creating separate domains; while other loops have a function in the expression of genes. Loops (chromatin proximity) of the latter type are frequent within topological domains and much less so between chromatin located in different topological domains.

Regulatory DNA elements interact with each other and the genes within a domain and form complex interaction networks. Changes within these elements and their interactions (in addition to mutations in the genes) are responsible for changes in gene expression, which in turn is responsible for the differences between individuals of a species or causing disease. Thus these elements have become important for the diagnosis and treatment of disease. However, these regulatory networks are still relatively unknown, although significant effort has recently been put into the elucidation of their function.

Regulatory elements are short fragments which contain one or more binding sites for transcription factors which activate or repress genes. Regulatory elements are often located far from their target genes and, although they can be recognized by the binding of particular factors such as p300 or chromatin modifications, it is often not clear with which genes they interact. In the spatial organization of the genome, they are in close proximity with their target genes. For example in polydactyly, although the enhancer affected is located about 1 Mbp away from the affected growth factor gene Shh on a linear map of the genome it is closely associated with the gene in the 3D space of the nucleus.

Although it was already clear that regulatory elements regulate genes by looping, chromosome conformation capture (3C) brought a revolution in the field by allowing the rapid identification of such interactions. The basic principal of the 3C technique is that the close proximity of DNA fragments in the nuclear space can be detected by crosslinking followed by restriction enzyme digestion, ligation and amplification of the ligated product. A number of 3C types techniques have subsequently been developed which provide more information about the interactions and the way the genes are regulated: 3C/3C-qPCR; 3C-seq/4C-seq; 4C (3C-on-a chip); 5C (3C carbon copy); and Hi-C.

Each of these methods is associated with various advantages and disadvantages (Table 1). 3C and 4C techniques are quite laborious, require prior knowledge of the locus and are restricted to detecting the interactions from a specific viewpoint. In order to analyse several interactions, a number of different viewpoints have to be used requiring separate analyses. The 3C and 4C techniques do not yield genome wide data.

The 5C and HiC techniques are more advanced. 5C is highly demanding in primer design and allows the analysis of a number of separate interactions, but does not give genome wide coverage. HiC is very expensive as it requires a very large amount of sequencing in order to analyse the whole genome without offering high resolution analysis (normally 40 Kbp). The most recent HiC method of analysis uses a new algorithm and provides a resolution of 10 Kbp. However, it requires an enormous amount of sequencing (3.4 billion mapped paired-end reads from 6 biological replicates). Sequencing on this scale is not available to most research groups. Also, the interest very often relates to a specific question involving a limited set of specific loci or domains, for example the regions involved in genomic alterations in disease, which means that a significant proportion of the sequencing performed by the HiC method is superfluous for these applications.

There is thus a need for an improved method for analysing the interaction of nucleotide sequences in three-dimensional chromatin structure which does not suffer from the above limitations.

TABLE 1

Comparison between different chromatin conformation capturing techniques

| Method | Applications | Advantages | Disadvantages |
| --- | --- | --- | --- |
| 3C-qPCR | One-to-one | Simple analysis | Laborious, requires knowledge of the locus and proper controls |
| 3C-seq/4C-seq | One-to-all | Allows wide coverage, good resolution, good signal to noise ratio | Restricted to single viewpoint per experiment when multiplexing several viewpoints, the analysis requires extra bioinformatics expertise |
| 3C-on-chip (4C) | One-to-all | Relatively simple data analysis | Poor signal to noise ratio, difficult to obtain genome wide coverage, analysis requires some bioinformatics expertise |
| 5C | Many-to-many | Identifies interactions between many individual fragments | Very laborious, no genome wide coverage, primer design can be challenging. |
| HiC | All-to-All | Explores the genome wide interactions between all individual fragments | Very expensive, requires a large sequence effort to obtain sufficient coverage, ~10-40 Kbp resolution, requires advanced bioinformatics expertise, repetitive sequences are excluded from the analysis |

DESCRIPTION OF THE FIGURES

The patent or application file contains at least one drawing executed in color. Copies of this patent or patent application publication with color drawing(s) will be provided by the Office upon request and payment of the necessary fee.

Isolated cross-linked chromatin is digested and ligated under diluted conditions to favour links between restriction fragments in close proximity. After decrosslinking and a secondary digestion, the overhangs are repaired followed by adaptor ligation. The adaptor contains sequences required for the sequencing method e.g. paired end Illumina or optionally a short address sequence. Different addresses would be used in different samples to allow multiplexing (hybridisation of different samples to the same set of oligonucleotide probes) where the address sequence allows the matching of a sequence with the sample it was derived from. The resulting library(ies) is/are hybridized to a set of unique oligonucleotide probes on an array or oligonucleotide probes in solution that can be captured on beads. The unique oligonucleotide probes (green squiggles) are located as close as possible to the first restriction site. The hybridized DNA is eluted and contains the library of all interactions from the selected area of the genome and is pair-end sequenced on an Illumina HiSeq2000 followed by bionformatical analysis and visualization of the interactions (i.e. sequences in close proximity). Vertical black lines depict primary restriction enzyme cleavage sites. Orange small vertical lines depict secondary restriction enzyme cleavage sites.

Figure 1:
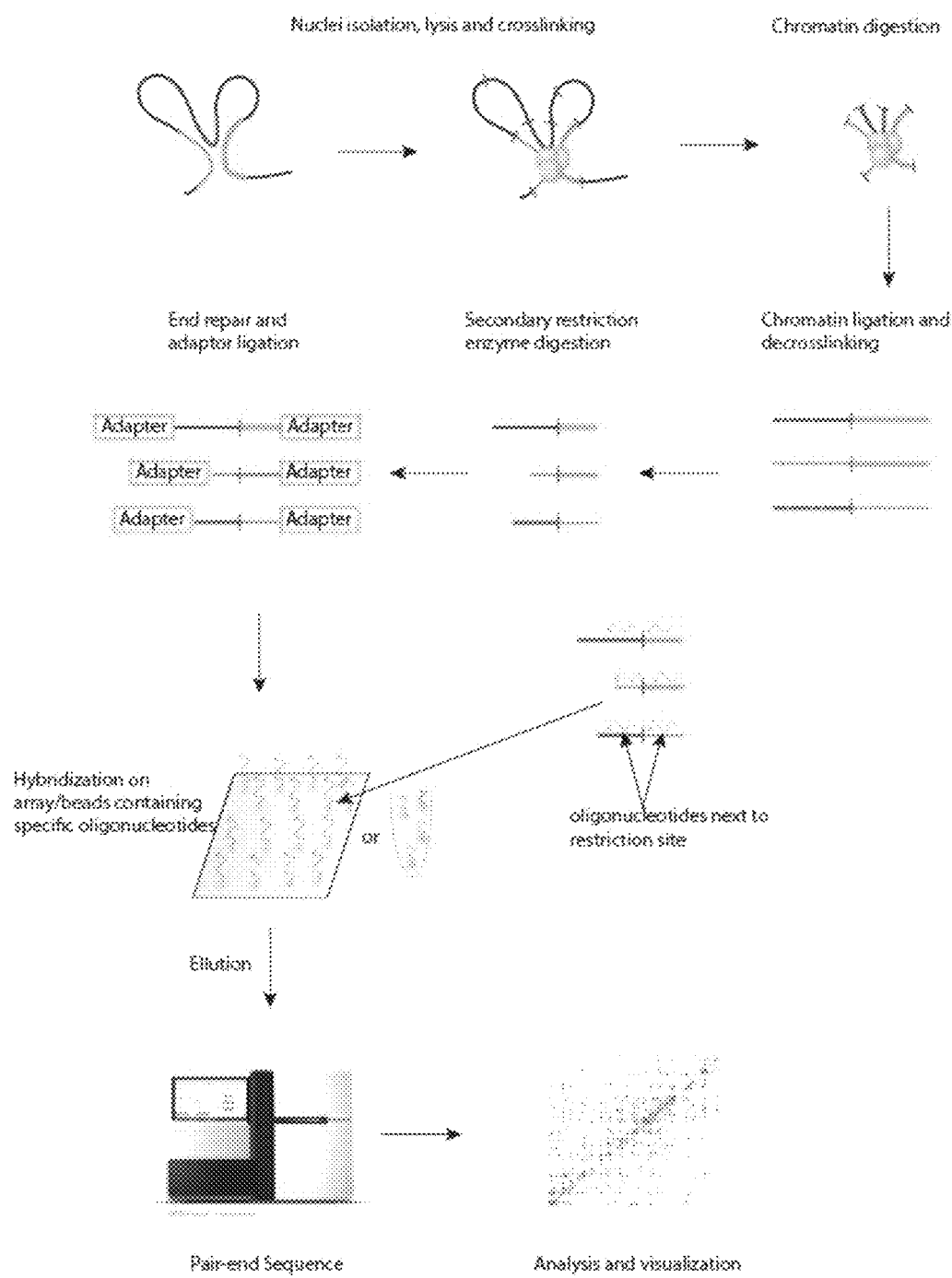
FIG. 1: Overview of the T2C procedure
Figure 2A:
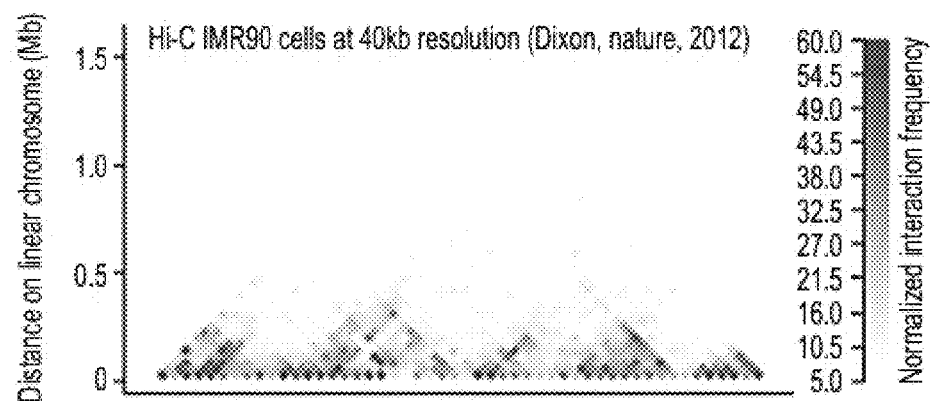
Figure 2B:
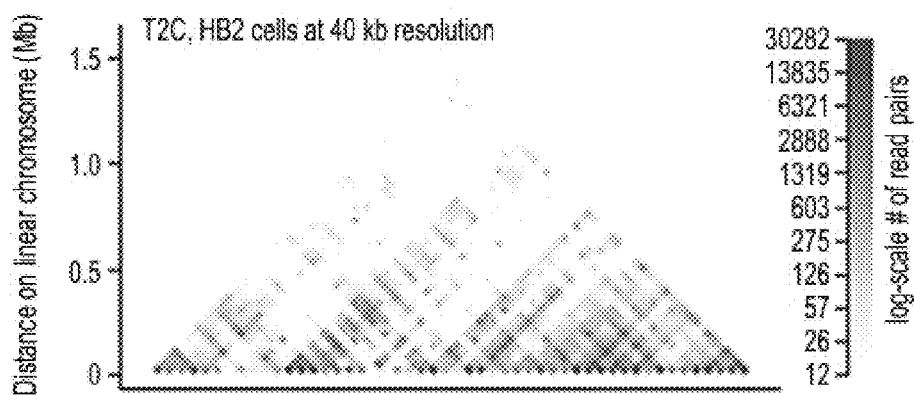
Figure 3A:
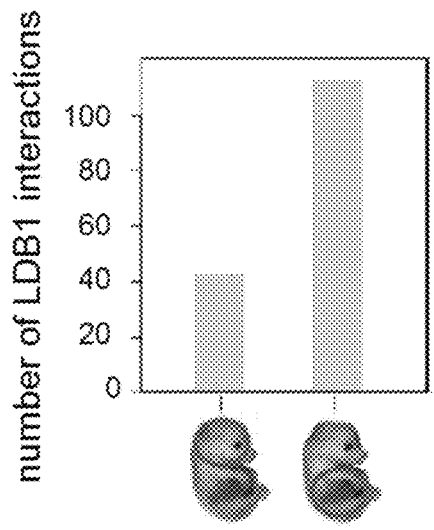
Figure 3B:
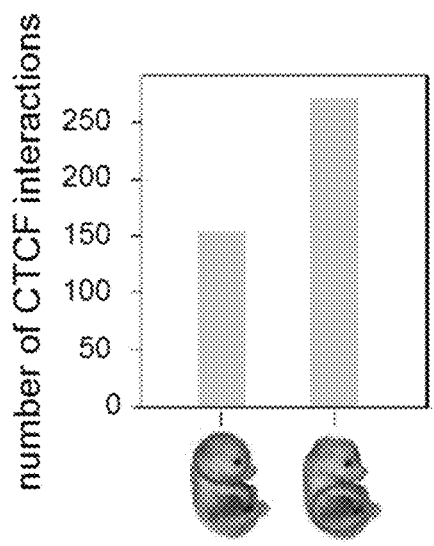
Figure 3C:
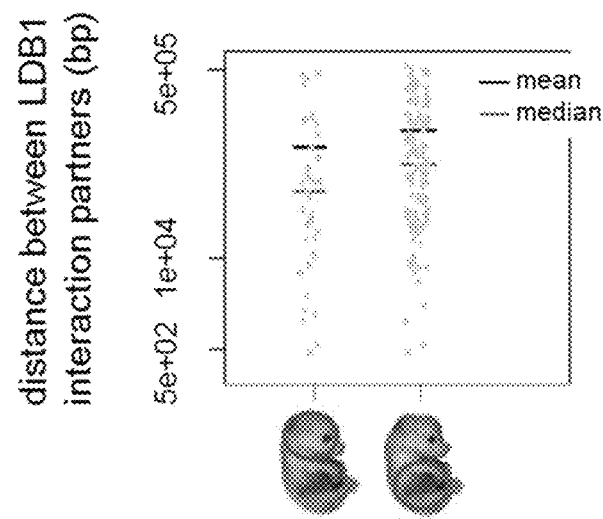
Figure 3D:
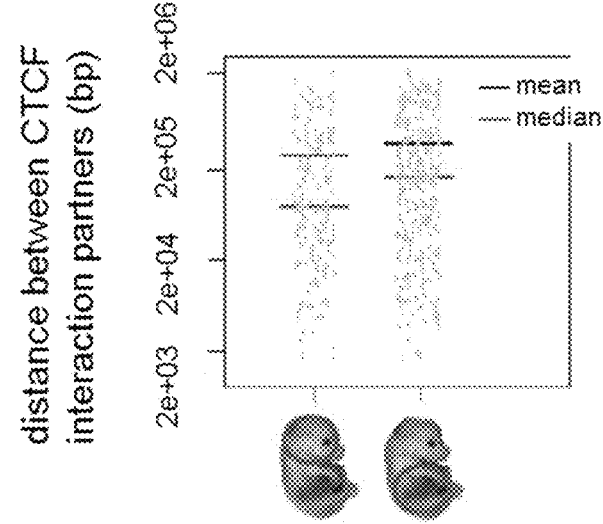
Figure 4:
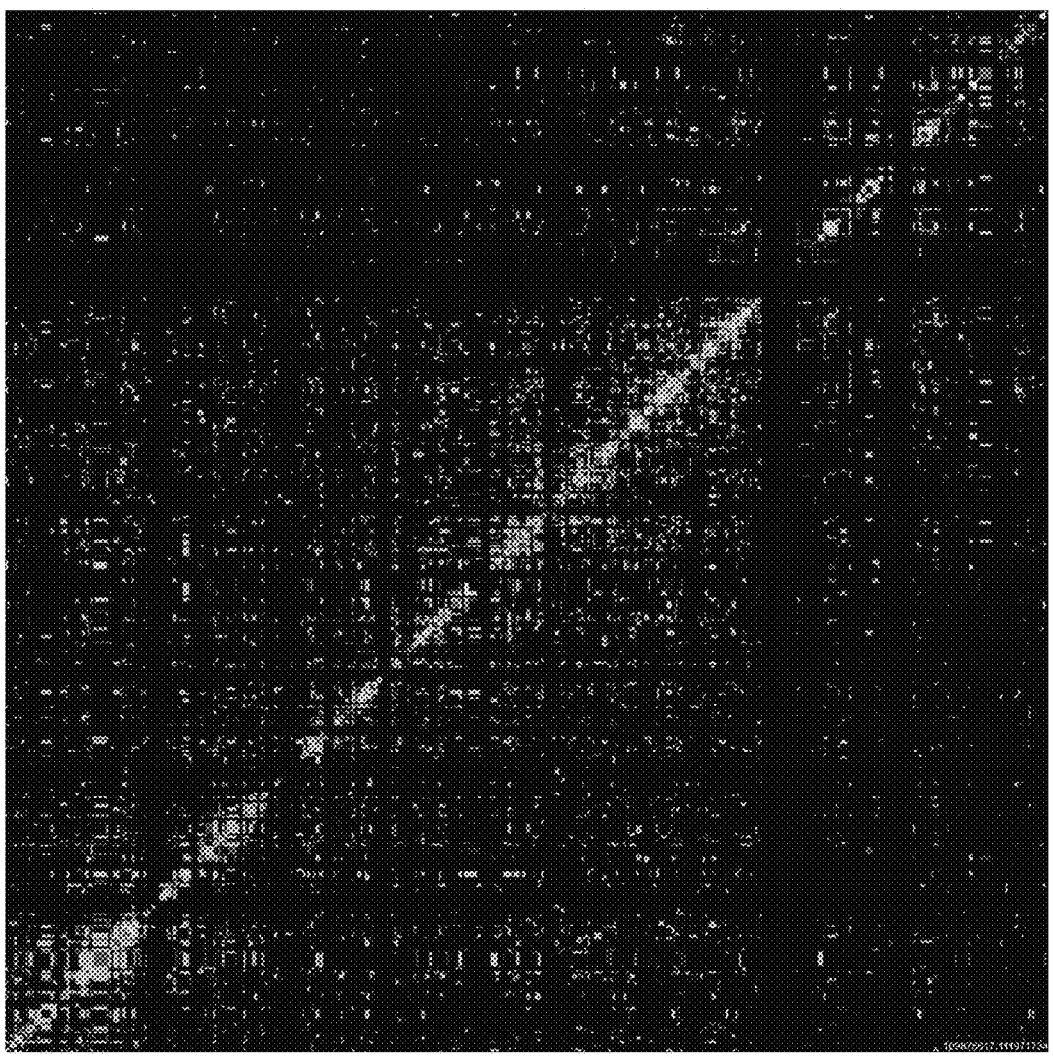
Figure 5:
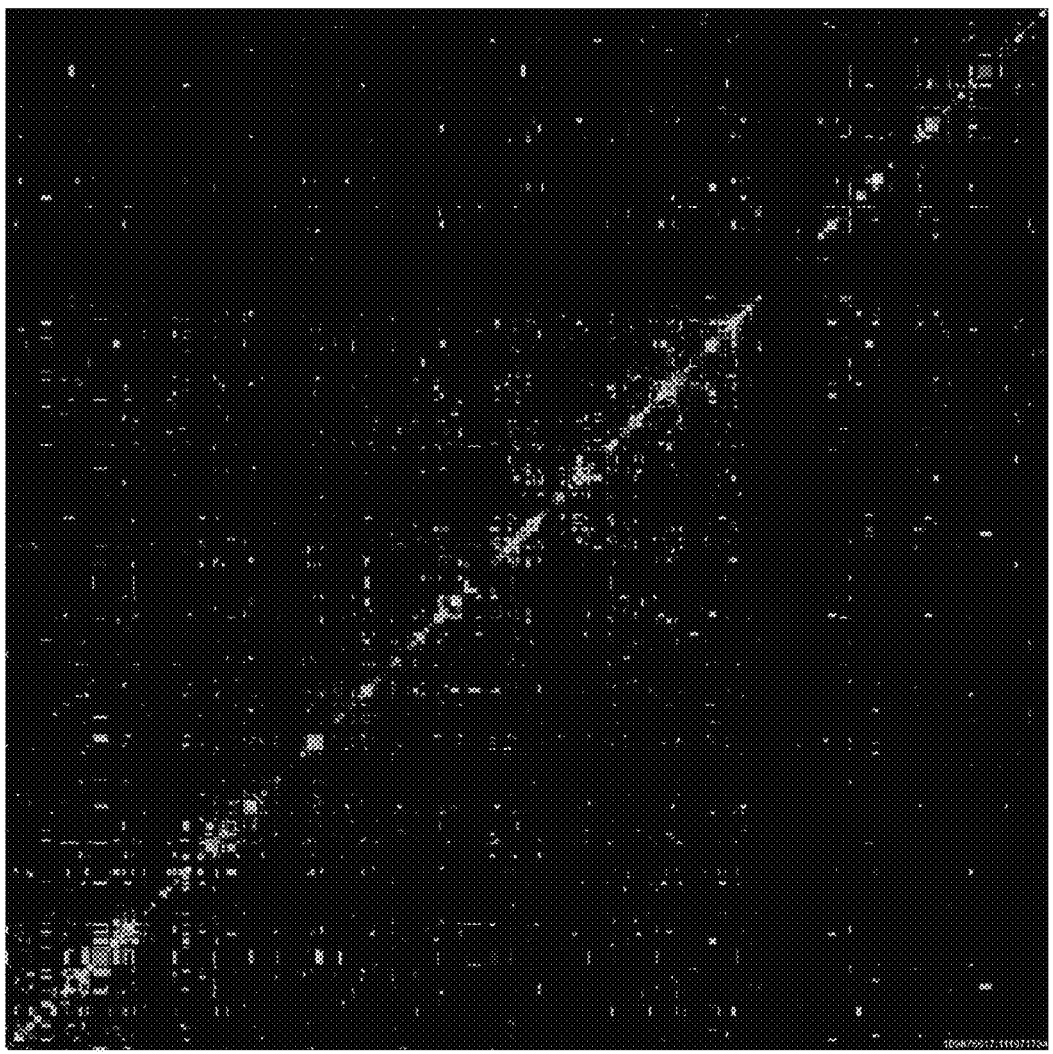

FIGS. 2A-2B: Comparison of interactions detected by T2C for the human chr11p15.5 region with Hi-C data and 4C data 2A shows Hi-C data generated for IMR90 cells covering the H19/IGF2 region of interest, presented at 40 Kbp resolution.

2B shows Interactions observed by T2C in HB2 cells are presented using the same 40 kbp bins as in (A). The overall topological domain pattern observed by the two methods is similar. The left vertical axis depicts distance on linear chromosome in Mb. The right vertical axis depicting-scale number of read pairs.

The left vertical axis depicts Distance (Mb) on linear chromosome. The right vertical axis depicts Normalized Interaction Frequency.

FIGS. 3A-3D: The mean, median and the number of interactions for the LDB1 or CTCF only containing fragments.

The number of LDB1 (FIG. 3A) and CTCF (FIG. 3B) interactions is lower in mouse fetal brain when compared to primary erythroid cells. Furthermore, the mean and the median of the distance between either LDB1 (FIG. 3C) or CTCF (FIG. 3D) interaction partners is lower in mouse fetal brain cells when compared to mouse primary erythroid cells.

Figure 6:
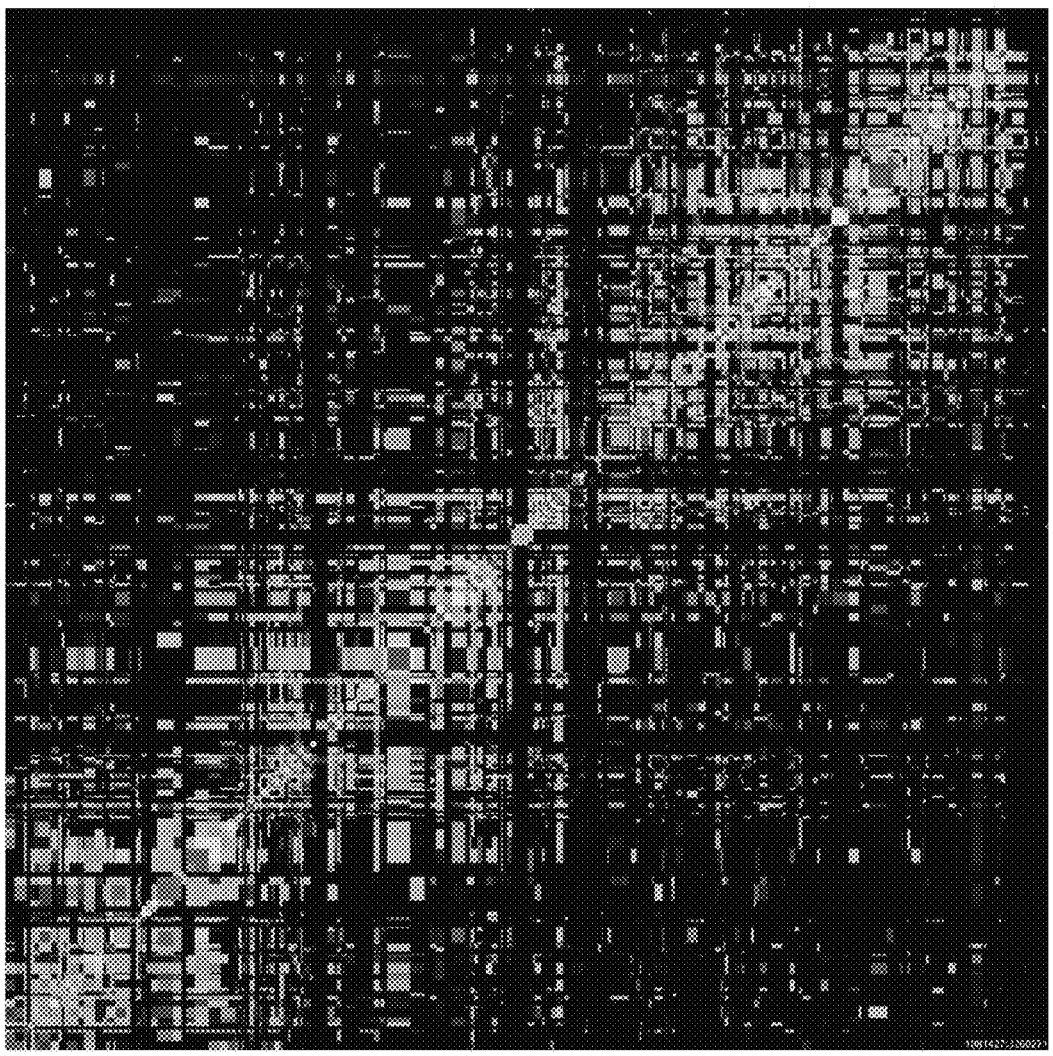
Figure 7:
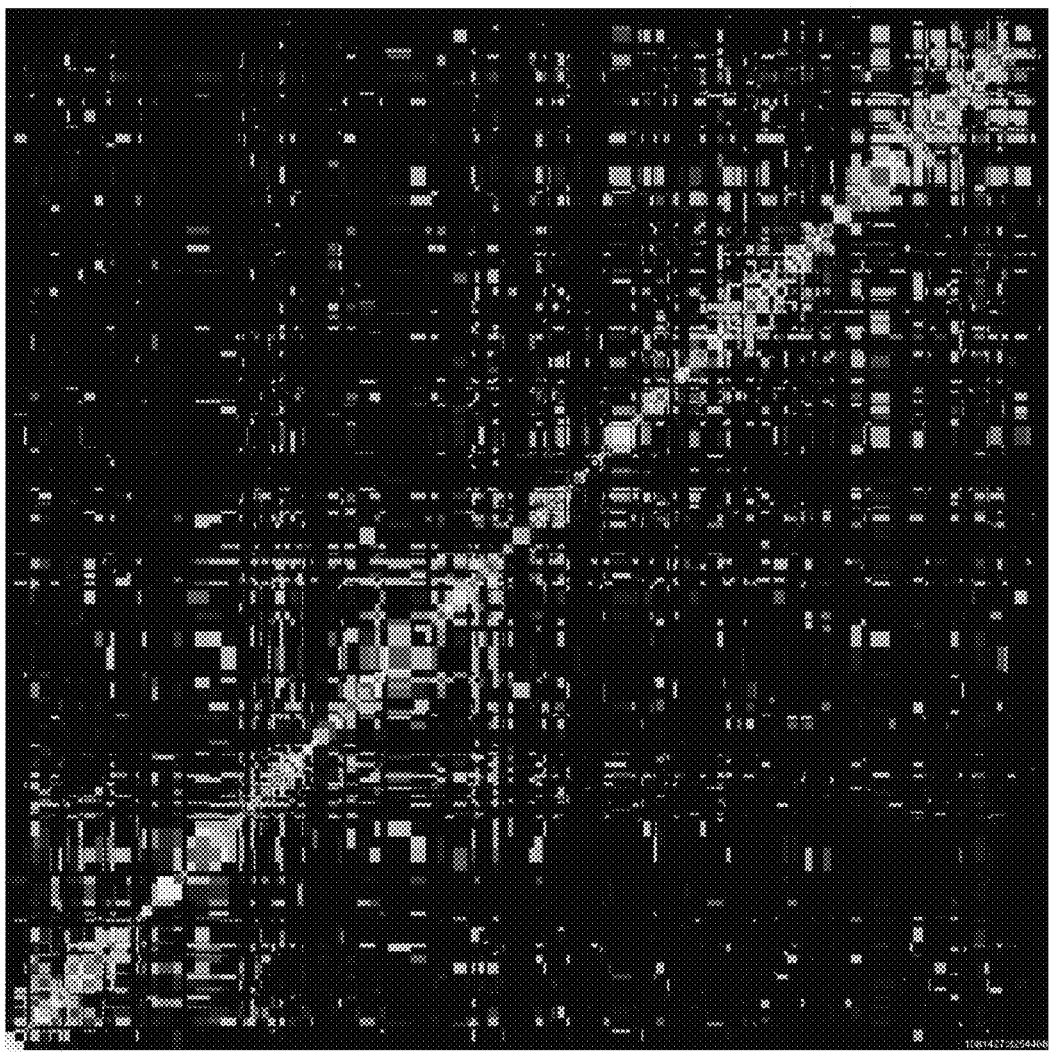
Figure 8:
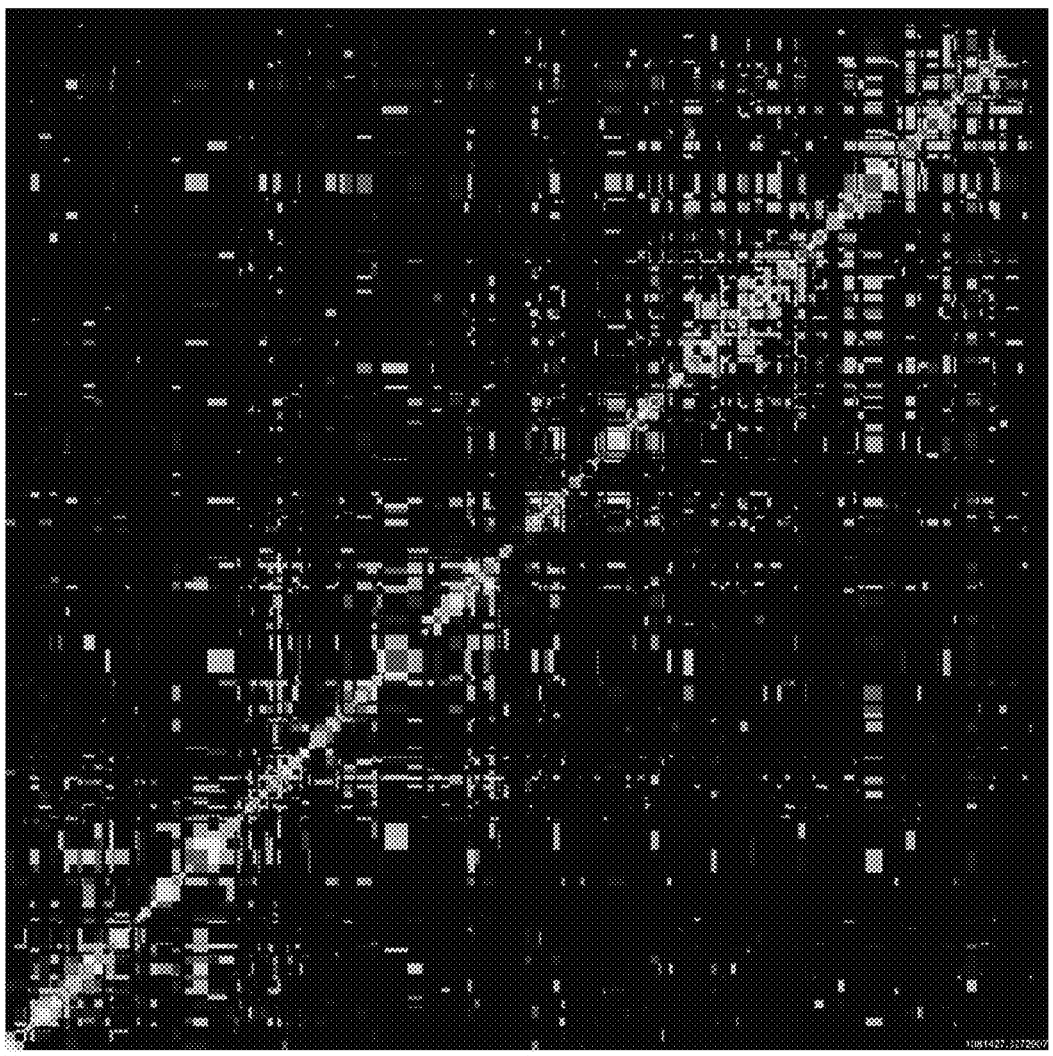

FIGS. 4 to 8: Visualization of interaction matrices for mouse fetal brain (FIG. 4), mouse fetal liver (FIG. 5), human HB2 (FIG. 6), human TEV (FIG. 7), and human HEV (FIG. 8) cells all for ~2 Mbp region and using in the visualization a logarithmic frequency range and a rainbow colour code. The pictures show clearly the superior resolution and quality of T2C and with a direct visual readout, that the genome is organised in subchromosomal domains, consisting of chromatin loops which form loop aggregates/rosettes. This is species specific (compare FIGS. 4 and 5, with FIGS. 6-8), tissue/cell specific (FIGS. 4 and 5 and FIGS. 6-8), depends on the activity of genes (FIGS. 4, 5, 6, and 7), and the presence of structurally relevant proteins such as cohesin (FIGS. 6 and 7). Thus, the structure also depends to disease states in which genetic or structural changes, change the interactions (FIGS. 4 and 5, or FIGS. 7 and 8).

FIGS. 9A-9B: Simulated chromatin models description and relation/evaluation of spatial distances between genomic markers, in the Immunoglobulin Heavy Chain Locus and the Prader-Willi/Angelmann Syndrome region:

FIG. 9A: Volume rendered images of simulated Random-Walk/Giant-Loop and Multi-Loop-Subcompartment Models. As a starting conformation with the form and size of a metaphase chromosome (top), rosettes were stacked (alpha). From such a starting configuration, interphase chromosomes in thermodynamic equilibrium, were decondensed by Monte-Carlo and relaxing Brownian Dynamics steps. A volume rendered image of the simulated Random-Walk/Giant-Loop model containing large loops (5 Mbp) is shown (left; beta). Note that the large loops do not form distinct structures but intermingle freely (left; beta). In contrast, in a volume rendered image of the simulated Multi-Loop-Subcompartment Model, containing 126 kbp sized loops and linkers, the rosettes form distinct chromatin territories in which the loops do not intermingle freely (middle; gamma In an image of the simulated RW/GL model containing 126 kbp loops and 63 kbp linkers, again distinct chromatin territories are formed but in contrast to the MLS model no subcompartments form (right; delta). FIG. 9B: Random-Walk Giant Loop and Multi-Loop-Subcompartment Models: indicates the RW/GL model in which large loops are attached to a non-DNA backbone. shows the simulated model containing a chromatin linker between loops. MLS model is shown containing 126 kbp loops and linkers with individual rosettes spanning 1-2 Mbp.

SUMMARY OF ASPECTS OF THE INVENTION

The present inventors have developed a new technique entitled 'Targeted-Chromatin Capture' (T2C) in order to overcome the disadvantages of 5C and HiC.

T2C employs a selective enrichment of the 3C ligation products from one or more region(s) of interest in order to identify the interactions within a domain and the compartmentalization of one or several specific regions of the genome. The region of interest may be a large (e.g. many megabase-sized) continuous genomic region or may alternatively be a collection of smaller regions (a few megabases each).

Every captured restriction fragment can be used as a "viewpoint", identifying the nucleotide sequences which interact with that sequence in the three-dimensional genome structure. The output of T2C provides a local interaction map with restriction fragment-level resolution. The method involves considerably less sequence efforts and less intricate bioinformatics analysis than the Hi-C method. The method also is not hampered by the limitations of the 5C method since T2C also identifies interactions of the fragments within the targeted region(s) with regions outside of the targeted region(s).

Thus, in a first aspect, the present invention provides a method for analysing the interaction of one or more nucleotide sequence(s) from one or more region(s) of interest with other nucleotides sequences in a three-dimensional DNA structure, comprising the steps of:
(a) providing a sample of cross-linked DNA;
(b) digesting the cross-linked DNA with a first restriction enzyme;
(c) ligating the cross-linked nucleotide sequences;
(d) reversing the cross-linking;
(e) fragmenting the ligated molecules from (d);
(f) hybridising the fragments from (e) to one or more oligonucleotides representing the sequences which are adjacent to the cleavage site of the first restriction enzyme in order to enrich for the ends of the nucleotide sequences that have been ligated to another nucleotide sequence in step (c); and (g) analysing the nucleotide sequence of the enriched fragments in order to identify the nucleotide sequences involved in interaction(s).

The method may be used for analysing the interaction of one or more nucleotide sequence(s) from one or more genomic region(s) of interest with other nucleotides sequences in three-dimensional chromatin structure.

The first restriction enzyme may be any restriction enzyme that recognises a 6-8 bp recognition site.

The first restriction enzyme may be selected from the group consisting of BglII, HindIII, EcoRI, BamHI, SpeI, PstI and NdeI.

In step (e) of the method, the ligated molecules may be fragmented by digestion with a second restriction enzyme, such as an enzyme recognises a 4 or 5 bp nucleotide sequence recognition site or even a dinucleotide sequence.

The second restriction enzyme may be selected from the group consisting of TspEI, MaeII, AluI, NlaIII, HpaII, FnuDII, MaeI, DpnI, MboI, HhaI, HaeIII, RsaI, TaqI, CviRI, MseI, Sth132I, AciI, DpnII, Sau3AI and MnlI.

Alternatively, in step (e), the ligated molecules may be fragmented by mechanical means, such as shearing or sonication.

Alternatively the first restriction enzyme may be any restriction enzyme that recognizes a 4-6 base pair recognition site (where the 6 bp is a degenerate sequence) in which case the second restriction enzyme would be replaced by a non specific nuclease or mechanical means of shearing. This would result in a higher number of oligonucleotides for hybridisation (see below) and a higher resolution of the interactions, because there are more primary restriction fragments.

In step (f), the one or more oligonucleotide probe(s) may be spotted on a microarray or captured on beads, or alternatively be present in solution, which are later captured on beads.

The oligonucleotide probe(s) may recognise a sequence adjacent to the restriction site of the first restriction enzyme, such as a sequence within 100 bp of the restriction site of the first restriction enzyme.

In step (f), the nucleotide sequence fragments may be hybridised to a set of oligonucleotide probes which comprises a plurality of oligonucleotides, each of which hybridises to a sequence which is adjacent to the digestion site of the first restriction enzyme on a nucleotide sequence from the genomic region of interest.

The set of oligonucleotide probes comprises probes specific to substantially all the restriction fragments obtainable by treating the genomic region(s) of interest with the first restriction enzyme.

An adapter sequence may be ligated to one or both ends of the nucleotide sequence fragments from (e) before step (f) such that the ligated nucleotide sequence fragments may be captured on the array by hybridisation, amplified and/or sequenced or allow the distinction of different samples hybridised to the same sets of oligonucleotide probes. The adapter may contain a specific address sequence that allows one sample to be distinguished from another sample. All sequences with a particular address sequence are then known to originate from one particular sample.

Step (g) of the method may involve high throughput sequencing of the enriched nucleotide sequence fragments.

Step (g) may be followed by bioinformatical analysis and/or visualisation of the interaction(s).

The region of interest (such as the genomic region of interest) may comprise a genetic locus of interest.

The region of interest may be about 1-50 MB in length altogether.

The method of the present invention may be used to analyse the interaction of a particular genetic element with other nucleotides sequences in three-dimensional structure, if in step (g) only the sequence of the enriched nucleotide sequence fragments comprising the particular genetic element are analysed in order to identify the nucleotide sequence(s) involved in interaction(s) with the genetic element.

The genetic element may comprise a binding site for a transcription factor or an insulator or barrier element.

The genetic element may be in the region of interest, for example an element frequently involved in or close to a genomic region that is rearranged or deleted in disease.

The method of the present invention may also be used to determine the expression status of a gene by analysing the number, type or density of interactions in a region of interest which comprises the gene.

The method may be used to compare gene activity between two samples, by analysing both samples and comparing the number, type or density of interactions in a region of interest.

The method may be used to identify which protein, such as a transcription factor is responsible for particular interactions.

The samples may, for example be: from different tissues from the same subject; from a single subject over different time points; from equivalent tissues from different subjects (e.g. healthy/diseased/suspected diseased subjects).

The method may be used to identify one or more DNA-DNA interactions that are indicative of a particular disease state by analysing a sample of cross-linked DNA from a diseased and a non-diseased cell, a difference between the interaction of nucleotides sequences in three-dimensional chromatin structure between the DNA sequences from the diseased and non-diseased cells showing that the DNA-DNA interaction or pattern of DNA-DNA interactions is indicative of a particular disease state.

The method of the invention may be used in the diagnosis or prognosis of a disease or syndrome caused by or associated with a change in a DNA-DNA interactions. In this respect, step (a) involves providing a sample of cross-linked DNA from a subject; and and step (g) involves comparing the interaction between the DNA sequences with that of an unaffected control; a difference between the control and the subject being indicative that the subject is suffering from the disease or syndrome or being indicative that the subject will suffer from the disease or syndrome.

The disease may be an inherited genetic disease, or a somatic genetic disease such as cancer.

In a second aspect, the invention also provides an assay method for identifying one or more agents that modulate the three dimensional structure of DNA comprising the steps of:
(a) contacting a sample with one or more agents; and
(b) performing the method of the first aspect of the invention, wherein step (a) comprises providing cross-linked DNA from the sample;
wherein a difference between (i) DNA interactions in the presence of the agent and (ii) DNA interactions in the absence of the agent is indicative of an agent that modulates the three dimensional structure of DNA.

T2C offers significant advantages over known 5C or HiC methods, for example:
- every restriction fragment as opposed to 5C can serve as a 'viewpoint' and all their interactions can be identified whether they are over short or long distances or to other chromosomes
- the compartmentalization of the genome can be identified in the regions of interest without requiring the large sequence effort that was required for HiC, thus reducing cost significantly
- a better coverage and resolution of the locus is obtained when compared to other techniques. The resolution of the T2C is based on the restriction enzyme used but is often of the order of 1-10 Kb (average 4-5 kb for a 6 bp recognition restriction enzyme). This provides a significantly better resolution than the usual 40 Kbp bins obtained with the usual HiC.

DETAILED DESCRIPTION

The present invention relates to a method for analysing the interaction between nucleotides sequences in a three-dimensional DNA structure.

Three-Dimensional DNA Structures

The term "three dimensional DNA structure" means a structure comprising DNA which has a higher order structure that the DNA double helix, forming, for example, loops and folds, similar to the higher order structure of an amino acid sequence in a protein molecule. The structure may be composed solely of DNA, or may comprise in addition other molecules, such as proteins. Chromatin is an example of a complex between DNA and proteins.

The method of the invention is ideally suited for analysis of the three dimensional chromatin architecture of genomes.

The primary functions of chromatin are 1) to package DNA into a smaller volume to fit in the cell, 2) to provide anchor points on the DNA to allow mitosis, and 4) to control gene expression, DNA replication and repair. The most abundant protein components of chromatin are histones that compact the DNA.

The structure of chromatin depends on several factors. The overall structure depends on the stage of the cell cycle: during interphase the chromatin is structurally loose to allow access to RNA and DNA polymerases that transcribe and replicate the DNA. The local structure of chromatin during interphase depends on the genes present on the DNA: DNA coding genes that are actively transcribed are more loosely packaged and are found associated with RNA polymerases (referred to as euchromatin) while DNA coding inactive genes are found associated with structural proteins and are more tightly packaged (heterochromatin). Epigenetic chemical modification of the structural proteins in chromatin also alter the local chromatin structure, in particular chemical modifications of histone proteins by methylation and acetylation. As the cell prepares to divide, i.e. enters mitosis or meiosis, the chromatin packages more tightly to facilitate segregation of the chromosomes during anaphase.

In the nucleus of eukaryotic cells, interphase chromosomes occupy distinct chromosome territories. Recently large megabase-sized local chromatin interaction domains have been identified, termed "topological domains" (Dixon et al (2012, Nature 485, 376-380). These domains correlate with regions of the genome that constrain the spread of heterochromatin. The domains are stable across different cell types and highly conserved across species, indicating that topological domains are an inherent property of mammalian genomes.

The topological domains also interact with each other suggesting a possibly higher order structure of the genome into a series of rosette like structures.

The method of the invention may be used to identify and characterise topological domains or higher order structures within a genome, chromosome or part thereof.

The spatial organisation of the genome is intimately linked to its biological function, so it is important to understand higher order genomic structure.

Although the method of the invention is ideally suited for analysis of the three dimensional chromatin architecture of genomes, it can be applied to analyse nucleotide sequence interaction in any three-dimensional structure.

Nucleic acids, such as DNA, can spontaneously form a "quaternary structure" with itself, other nucleic acids and other molecules, such as proteins. The method of the invention can be used to analyse the three-dimensional architecture of any nucleic acid-containing structure. For example the method could be used to investigate and verify the hierarchical assembly of artificial nucleic acid building blocks used in DNA nanotechnology.

Region of Interest

The present invention involves analysing the interactions between nucleotide sequence(s) in a region of interest with other nucleotide sequences.

The region of interest may be a genomic region of interest within one (or more) chromosomes.

The region of interest may comprise a particular genetic locus of interest. A genetic locus is the specific location of a gene or DNA sequence or position on a chromosome. The genomic region of interest may comprise a particular locus, such as the sequence of a particular gene, together with one or both flanking regions. The region of interest may, for example, comprise the sequence of about 1, 2, 3 or 4 MB on both sides of the gene.

The "other nucleotide sequences" i.e. the nucleotide sequences with which the nucleotide sequences within the region of interest interact, may themselves be located in the region of interest, or they may be from other regions, such as other parts of the same chromosome(s) of from a different chromosome. Interactions with such regions may change in case of disease when the regulation of genes has changed or when genes are lost.

DNA

The 3D DNA structure may comprise genomic DNA—consisting of or comprising one or more genomic loci.

Method

The method of the invention includes the following steps:
(a) providing a sample of cross-linked DNA;
(b) digesting the cross-linked DNA with a first restriction enzyme;
(c) ligating the cross-linked nucleotide sequences; and
(d) reversing the cross linking.

These first four steps of the method of the invention are analogous to those of Chromosome Conformation Capture (3C) which is described in Dekker et al (2002) Science 295:1306; and 4C (Capture and Characterise Colocalised Chromatin), which is described in WO 2007/004057.

A 3C-like template may be prepared using known methods, such as the method described by Splinter et al., (2004) *Methods Enzymol.* 375, 493-507. Briefly, a sample—such as cells, tissues or nuclei—is fixed using a cross-linking agent—such as formaldehyde. The primary restriction enzyme digestion is then performed such that the DNA is digested in the context of the cross-linked nucleus. Intramolecular ligation is then performed at low DNA concentrations, which favours ligation between cross-linked DNA fragments (ie. intramolecular ligation) over ligation between non-cross-linked DNA fragments (ie. intermolecular or random ligation). Next, the cross links are reversed and the DNA can be purified. The 3C template that is yielded contains restriction fragments that are ligated because they were originally close in the nuclear space.

Since a primary restriction enzyme is used to digest the DNA prior to the intramolecular ligation step, an enzyme recognition site for the primary restriction enzyme will separate the first (target) nucleotide sequence and the nucleotide sequence that has been ligated. Accordingly, the primary restriction enzyme recognition site is located between the first (target) nucleotide sequence and the ligated nucleotide sequence (ie. the ligated second sequence).

Cross-Linking

Cross-linking agents—such as formaldehyde—can be used to cross link proteins to other neighbouring proteins and nucleic acid. Thus, two or more nucleotide sequences can be cross-linked via proteins bound to (one of) these nucleotide sequences. Cross-linking agents other than formaldehyde can also be used in accordance with the present invention, including those cross-linking agents that directly cross link nucleotide sequences. Examples of agents that cross-link DNA include, but are not limited to, UV light, mitomycin C, nitrogen mustard, melphalan, 1,3-butadiene diepoxide, cis diaminedichloroplatinum(II) and cyclophosphamide.

Suitably, the cross-linking agent will form cross-links that bridge relatively short distances—such as about 2 Å—thereby selecting intimate interactions that can be reversed.

Cross-linking may be performed by, for example, incubating the cells in 2% formaldehyde at room temperature—such as by incubating $1 \times 10^7$ cells in 10 ml of DMEM-10% FCS supplemented with 2% formaldehyde for 10 min at room temperature.

Digestion with Restriction Enzyme

The cross-linked DNA is digested with a first restriction enzyme.

Restriction endonucleases are enzymes that cleave the sugar-phosphate backbone of DNA. In most practical settings, a given restriction enzyme cuts both strands of duplex DNA within a stretch of just a few bases. The substrates for restriction enzymes are sequences of double-stranded DNA called recognition sites/sequences.

The length of restriction recognition sites varies, depending on the restriction enzyme that is used. The length of the recognition sequence dictates how frequently the enzyme will cut in a sequence of DNA.

Restriction enzymes which recognise a 4 bp sequence of DNA, together with their restriction sites, include: AATT (TspEI), ACGT (MaeII), AGCT (AluI), CATG (NlaIII), CCGG (HpaII), CGCG (FnuDII), CTAG (MaeI), GATC (DpnI, DpnII, Sau3AI & MboI), GCGC (HhaI), GGCC (HaeIII), GTAC (RsaI), TCGA (TagI), TGCA (CviRI), TTAA (MseI), CGCG (Sth132I), CCGC (AciI) and CCTC (MnII)

Restriction enzymes which recognise a 6 bp sequence of DNA, together with their restriction sites, include: AACGTT (AcII), AAGCTT (HindIII), AATATT (SspI), ACATGT (BspLU11I), ACCGGT (AgeI), ACGCGT (MluI), ACTAGT (SpeI), AGATCT (BglII), AGCGCT (Eco47III), AGGCCT (StuI), AGTACT (ScaI), ATCGAT (ClaI), ATGCAT (AvaIII), ATTAAT (VspI), CAATTG (MfeI), CACGTG (PmaCI), CAGCTG (PvuII), CATATG (NdeI), CCATGG (NcoI), CCCGGG (SmaI), CCGCGG (SadII), CCTAGG (AvrII), CGATCG (PvuI), CGGCCG (XmaIII), CGTACG (SplI), CTCGAG (XhoI), CTGCAG (PstI), CTTAAG (AfIII), GAATTC (EcoRI), GACGTC (AatII), GAGCTC (SacI), GATATC (EcoRV), GCATGC (SphI), GCCGGC (NaeI), GCGCGC (BsePI), GCTAGC (NheI), GGATCC (BamHI), GGCGCC (NarI), GGGCCC (ApaI), GGTACC (KpnI), GTATAC (SnaI), GTCGAC (SalI), GTGCAC (ApaLI), GTTAAC (HpaI), TACGTA (SnaBI), TCATGA (BspHI), TCCGGA (BspMII), TCGCGA (NruI), TCTAGA (XbaI), TGATCA (BclI), TGCGCA (MstI), TGGCCA (BalI), TGTACA (Bsp1407I), TTATAA (PsiI), TTCGAA (AsuII) and TTTAAA (AhaIII).

Restriction enzymes which recognise a 7 bp sequence of DNA, together with their restriction sites, include: CCTNAGG (SauI), GCTNAGC (EspI), GGTNACC BstEII and TCCNGGA PfoI.

Restriction enzymes which recognise an 8 bp sequence of DNA, together with their restriction sites, include: ATTTAAAT (SwaI), CCTGCAGG (Sse8387I), CGCCGGCG (Sse232I), CGTCGACG (SgrDI), GCCCGGGC (SrfI), GCGATCGC (SgfI), GCGGCCGC (NotI), GGCCGGCC (FseI), GGCGCGCC (AscI), GTTTAAAC (PmeI) and TTAATTAA (PacI).

There are also restriction enzymes which recognise degenerate sequences which means that two or more bases are possible at a particular position in the recognition sequence effectively resulting in 3 or 5 bp sequences of DNA that is recognized. One can also use a combination of enzymes to effectively recognise 2 bp, for example the combination of HpyCH21V, MspI, HinPII and TaqI effectively recognizes the 2 bp sequence CG.

The first restriction enzyme (or combination of enzymes) may recognise a 2, 4, 5, 6, 7 or 8 bp sequence of DNA.

The first restriction enzyme may, in particular, be a 6-cutter, such as HindIII or BglII.

The second restriction enzyme (or combination of enzymes) may recognize a 2 or 4 bp sequence of DNA or be replaced by a nonspecific nuclease (in which case only a limited digestion would be applied) or mechanical fragmentation.

Ligation and Reversal of Cross-Linking

The digestion step is then followed by ligation under diluted conditions that favour intra-molecular interactions and joining of the DNA via the compatible ends.

Ligation may induced by the addition of a ligase enzyme.

The ligation reaction may be performed at a low DNA concentration, such as about 1-5 ng/µl.

Cross-linking may be reversed by the addition of an agent such as proteinase K.

Further Steps of the Method

The method of the invention may also involve:

e) fragmenting the ligated DNA, for example with a second restriction enzyme (such as a 4 bp recognition enzyme) or other nucleases or by mechanical shearing. In the latter cases the DNA ends may be repaired to become blunt-ended to allow the addition of an adapter sequence (f) ligating on an adapter sequence that contains a specific sequence that allows the distinction between samples (the other sample containing a linker with a different specific sequence) and/or sequences that allow hi-throughput sequencing g) hybridise the ligated sample to one oligonucleotide probe or set(s) of oligonucleotide probes representing one or more genomic loci. The one or set(s) of oligonucleotides are selected on the basis of their proximity to the first restriction site as in step (a) and their hybridisation temperature. The latter is dependent on their length and base composition. Different oligonucleotide probes in a set should have similar hybridisation/melting temperatures. Moreover they should be unique to prevent the hybridisation of repetitive DNA. The oligonucleotide probes can be attached to a solid surface or contain a tag such as biotin that allows capture on a solid surface preferably streptavidin beads.

(h) stringently wash the hybridised solid surface after hybridisation to remove the non hybridised material.
(i) elute the hybridised material
(j) sequence the hybridised material for example by paired end Illumina sequencing
(k) use bio-informatics to map the sequences back to the genome and generate a matrix of interaction Fragmentation The ligated DNA molecule may be fragmented by various methods known in the art, such as digestion with a second restriction enzyme or other nucleases; using radiation or heavy ions; or mechanical means such as sonication or shearing.

The second restriction enzyme should cut DNA more frequently than the first restriction enzyme used in step (b) of the method. The second restriction enzyme may recognise a shorter or more common stretch of DNA (recognition site) than the first restriction enzyme.

If the first restriction enzyme is a 6-8 bp cutter, the second restriction enzyme may be, for example, a 2 or 4-cutter.

The second restriction enzyme may, for example, be a 4-cutter such as Dpn II of NlaIII.

The second restriction enzyme (or combination of enzymes) may recognize a 2 or 4 bp sequence of DNA or be replaced by a nonspecific nuclease (in which case only a limited digestion would be applied) or mechanical fragmentation. There are a large number of non-sequence specific nucleases, such as Micrococcal nuclease or DNaseI.

Following mechanical methods, such as shearing, non specific nucleases or treatment using radiation or heavy ions, the ends of the nucleotide sequences may need to be 'repaired' by standard methods to allow the next steps.

Adapter

An adapter may be ligated to the ends of the fragments from step (e) for sequencing purposes, i.e. to enable sequence analysis for methods such as the Illumina method.

The adapter may comprise an address sequence. Different address sequences are used for different samples to allow multiplexing (hybridisation of different samples to the same set of oligonucleotide probes) where the address sequence allows the matching of a sequence with the sample it was derived from. Address sequences are useful when multiple samples or internal spiking is used.

It is preferable for the adapter sequence to be added before hybridisation. It is possible to add them on by ligation after hybridisation but it is likely to be less efficient as the DNA comes off the hybridisation as single stranded DNA.

Hybridisation

In step (f) of the method, the nucleotide sequence fragments are hybridised to one or more oligonucleotide probe(s) in order to enrich for fragments which comprise an interacting nucleotide sequence The oligonucleotide probes are attached to or can be captured on a solid support, such as an array or beads (see below).

The oligonucleotide probes are designed based on the sequence(s) from the region of interest, bearing in mind the position of the restriction sites of the first restriction enzyme.

Each oligonucleotide probe corresponds to a sequence located close to the first restriction site. The ligated DNA molecule made in step (d) of the method of the invention comprises different nucleotide sequences, joined at the restriction site of the first restriction enzyme. The different nucleotide sequences were "interacting" (i.e. in close enough proximity to be cross-linked) in the three dimensional structure. When the ligated molecule is fragmented, some fragments will be derived from a single nucleotide sequence, from internal fragmentation (e.g. internal digestion by the second restriction enzyme). Other fragments will be derived from both the interacting nucleotide sequences.

By selecting fragments which have a sequence which is located close to the first restriction site, the fragments are enriched for those which represent an "interacting fragment" i.e. comprise a portion of two nucleotide sequences joined at the at the restriction site of the first restriction enzyme by the ligation step (c).

Oligonucleotide Probes

Suitably, the oligonucleotide probes will be at least 15, 20, 25, 30 or 40 nucleotides in length.

The oligonucleotide probes are designed to be as close as possible to the restriction enzyme recognition site of the first restriction enzyme. The term "adjacent to" means that the oligonucleotide probes are designed such that they recognise a site within about 100 nucleotides—such as about 90, 80, 70, 60, 50, 40, 30, 20, 10, 9, 8, 7, 6, 5, 4, 3, 2 or 1 nucleotide(s) away from the first restriction enzyme recognition site.

If the region of interest has X recognition sites of the first restriction enzyme (RE1), digestion with RE1 will produce X+1 fragments. These fragments will have an RE1 recognition site at both ends, so it is necessary to design 2× oligonucleotide probes to encompass all fragments in the region of interest.

The library of oligonucleotide probes may comprise oligonucleotides specific to substantially all the restriction fragments obtained by treating the region(s) of interest with the first restriction enzyme. "Substantially all" in this context, means at least 60, 70, 80, 90, 95 or 99% of the restriction fragment-flanking sites.

Occasionally it is not possible to design an oligonucleotide probe representing one of the ends, for example:
(i) the sequence may be repetitive
(ii) the second recognition enzyme site (RE2) may be too close to the RE1 site
(iii) there is no RE2 site between two RE1 sites. (When non-specific nuclease or mechanical fragmentation is used, this does not apply).

If any of the above limitations apply, oligonucleotide probes to that particular RE1 restriction fragment or end thereof may be omitted from the set of oligonucleotide probes, but the oligonucleotide set would still contain oligonucleotide probes to "substantially all" of the RE1-flanking sites.

Analysis

Once the fragments have been enriched for those representing an "interaction", the nucleotide sequences involved in the interaction may be characterised by sequencing.

Pair-end sequencing may be carried our using known techniques, such as the Illumina system.

An adapter sequence may be ligated to one or both ends of the nucleotide sequence fragments from (e) preferably before or less preferred after step (f) such that the ligated nucleotide sequence fragments may be captured on an array, amplified and/or sequenced. The adapter sequence may provide an address to recognize a sample when several samples are analysed on the same array, i.e. multiplexing. It is possible to multiplex 8 samples in one lane of an Illumina machine presently yielding ±150 million sequence reads per lane.

In more detail, the fragments may be end repaired and A-tailed, and the indexed adapters ligated to the A-tailed DNA fragments.

The resulting adapter-modified DNA library may be captured, eluted and PCR amplified. In the method of the invention the fragments may not be PCR amplified prior to the enrichment step (step (f)).

Cluster generation and high-throughput sequencing may then be performed by known techniques (e.g. using the Illumina cluster reagents and a HiSeq 2000 sequencer).

The interaction frequencies may be visualised by producing a two dimensional heat map as previously described (Liberman-Aiden et al (Science 2009 326:289-293; Dixon et al (2012, as above). Interaction frequencies between any two loci can be visualised by identifying the point off the axis where diagonals originating from each locus intersect, in a manner similar to a linkage disequilibrium plot.

Each point on the map represents an interaction point between two fragments (two fragments in close proximity). The intensity of each interaction point on the map is relative to the frequency of interaction/proximity of the fragments which it represents. The points on the diagonal represent self-ligation effect as well as ligation to the immediately neighbouring fragments. The visualisation is basically a matrix analysis.

Sample

A sample may be any physical entity comprising DNA that is or is capable of being cross-linked. The sample may be or may be derived from biological material.

The sample may be or may be derived from one or more cells, one or more nuclei, or one or more tissue samples. The entities may be or may be derivable from any entities in which DNA—such as chromatin—is present. The sample may be or may be derived from one or more isolated cells or one or more isolated tissue samples, or one or more isolated nuclei.

The sample may be or may be derived from living cells and/or dead cells and/or nuclear lysates and/or isolated chromatin.

The sample may be or may be derived from cells of diseased and/or non-diseased subjects.

The sample may be or may be derived from a subject that is suspected to be suffering from a disease.

The sample may be or may be derived from a subject that is to be tested for the likelihood that they will suffer from a disease in the future.

The sample may be or may be derived from viable or non-viable patient material.

A standard sample may be added to each experimental sample (spiking) to allow better comparison between different sample as the samples may be normalised using the sequence reads of the spiking sample. The spiking sample may be from a different species than the experimental sample to allow spiking in the form of cells at the first step, alternatively the spiking sample may have its own address or be from a different species when spiking at later stages in the procedure.

Array

Typically, the set of oligonucleotide probes will be immobilised on a support or be captured on a solid support such as beads. Supports (eg. solid supports) can be made of a variety of materials—such as glass, silica, plastic, nylon or nitrocellulose. When attached to a solid support it is preferably rigid and have a planar surface. Supports typically have from about 1-10,000,000 discrete spatially addressable regions, or cells. Supports having about 10-1,000,000 or about 100-100,000 or about 1000-100,000 cells are common. The density of cells is typically at least about 1000, 10,000, 100,000 or 1,000,000 cells within a square centimeter. In some supports, all cells are occupied by pooled mixtures of oligonucleotide probes or a set of oligonucleotide probes. In other supports, some cells are occupied by pooled mixtures of probes or a set of oligonucleotide probes, and other cells are occupied, at least to the degree of purity obtainable by synthesis methods, by a single type of oligonucleotide.

For a restriction enzyme recognising a >6 bp recognition sequence, a single array of about 2×750,000 oligonucleotide probes can be used to cover, for example, the complete human or mouse genome, with 1 oligonucleotide probe at each side of each restriction site.

Oligonucleotide Probes in Solution

Oligonucleotide probes in solution may contain a moiety that can be captured on a solid surface, such as oligonucleotides containing a biotin that can be captured by streptavidin beads. Hybridisation in solution may be more efficient.

Capture May Take Place after Hybridisation

Hybridisation

The term "hybridisation" as used herein shall include "the process by which a strand of nucleic acid joins with a complementary strand through base pairing".

Nucleotide sequences capable of selective hybridisation will be generally be at least 75%, 85%, 90%, 95% or 98% homologous to the corresponding complementary nucleotide sequence over the length of the oligonucleotide probe. Selectivity is determined by the salt and temperature conditions during the hybridisation.

"Specific hybridisation" refers to the binding, duplexing, or hybridising of a molecule only to a particular nucleotide sequence under stringent conditions (e.g. 65° C. and 0.1× SSC {1×SSC=0.15 M NaCl, 0.015 M Na-citrate pH 7.0}). Stringent conditions are conditions under which a oligonucleotide probe will hybridise to its target sequence, but to no other sequences. Stringent conditions are sequence-dependent and are different in different circumstances. Longer sequences hybridise specifically at higher temperatures. Generally, very stringent conditions are selected to be about 5° C. lower than the thermal melting point (Tm) for the specific sequence at a defined ionic strength and pH. The hybridisation temperature is the temperature below the melting temperature (Tm) and the closer the hybridisation temperature is to the Tm the more stringent the hybridisation is, meaning that mismatched DNA sequences will not hybridise to each other. The oligonucleotide sequences should be in excess over the genomic DNA to ensure efficient, preferably complete and thereby quatitative hybridisation. Typically, stringent conditions include a salt concentration of at least about 0.01 to 1.0 M Na ion concentration (or other salts) at pH 7.0 to 8.3. Stringent conditions can also be achieved with the addition of destabilising agents—such as formamide or tetraalkyl ammonium salts.

The invention will now be further described by way of Examples, which are meant to serve to assist one of ordinary skill in the art in carrying out the invention and are not intended in any way to limit the scope of the invention.

EXAMPLES

Example 1—T2C Identifies Known Long-Range Interactions

To test the method and to compare it with other methods, the inventors first chose the IGF/H19 region on human chromosome 11 that has previously been used to study the role of cohesion and CTCF for chromosomal long-range interactions and for which Hi-C and 4C data are already available for comparison.

A set of array-based oligonucleotides were designed mapping near the ends of all the BglII fragments covering an approximately 2.1 Mbp region of the H19 locus, totaling 524 oligonucleotides corresponding to 344 BglII fragments. A number of BglII fragments did not allow the design of an oligonucleotide representing one of the ends because the sequence was either repetitive or the 4 bp recognition enzyme site (NlaIII) was too close to the BglII site or completely absent from the BglII fragment. The crosslinked BglII restricted DNA was ligated, decrosslinked, digested with NlaIII enzyme and hybridized to the oligonucleotide array after decrosslinking (see Methods).

Analysis of the sequenced ligation products first with a 40 kb binning of the genome as used for HiC (FIG. 2A) demonstrated that T2C (FIG. 2B) reveals a similar overall interaction pattern as observed by Dixon et al ((2012), as above) for IMR90 cells (interactions outside the area or with other chromosomes are also observed but not shown). This is also consistent with the previously observed conservation of overall architectural features like topological domains between different cell lines (FIGS. 2A and 2B).

However, with T2C, an interaction map at restriction fragment resolution was obtained, revealing a lot more detail with respect to the general chromatin organization of the region and contacts between genes and their regulatory elements. To compare this chromatin structure information of T2C the data were compared with 4C data and the 4C data obtained for a particular CTCF viewpoint were plotted next to the interaction data observed for the same viewpoint present in the T2C data.

Although there are some variations in the read coverage of the individual interactions, the same interactions can be observed by 4C and T2C. The T2C method therefore yields reproducible results, faithfully detects the fragments that interact (or are in close proximity), clearly reproduces the overall genomic structure in topological domains and gives resolution around the 4-5 kbp expected for a 6 bp recognition restriction fragment.

Example 2—T2C Identifies Different Interaction Networks Based on Different Biological Materials In order to also test whether different gene expression states can be detected in different biological tissues with different chromatin interactions, T2C was applied in in vivo mouse primary erythroid cells from mouse fetal liver and brain cells from E12.5 mice. The well-studied β-globin locus was used as an example in a region of ~2 MB around the gene. It is well established that as β-globin is expressed more highly in primary erythroid cells compared to fetal brain cells, a denser number of interactions is expected around the gene and between the gene and its locus control region (LCR) in this cell type. The β-globin region was digested with HindIII as the 6 bp enzyme and 799 oligonucleotide probes were designed to cover the ends of the HindIII fragments in the locus (724 fragments, many of which are repetitive) and after crosslinking re-digested with DpnII.

The analysis of the hybridised fragment after cleavage with DpnII showed 5 topological domains in the region of interest (~2 MB) in both mouse primary erythroid cells and mouse fetal brain cells with many interactions within each topological domain. The topological domains also interact with each other suggesting a possibly higher order stucture of the genome into a series of rosette like structures. Although the number of topological domains between the different biological materials appears to be the same the interactions within and between the topological domains appear to be less dense in mouse fetal brain cells comparing mouse primary erythroid cells. Zooming in on the all the β-globin region shows all the well-known interactions in the β-globin locus in the fetal liver material. The interactions such as between the β-globin promoter and LCR and between the LCR-3'HS1 are clearly visualised. These are absent from the fetal brain sample. Moreover, it is possible to identify new additional interactions further away than the ones reported until now for the β-globin promoter. These are located as far as ~1 Mbp from the β-globin promoter.

The interactions of the binding sites of an important regulatory transcription factor in fetal liver cells, the LDB1 complex or the structural factor CTCF, was also compared. LDB1 is highly enriched on the β-globin locus and its LCR in mouse primary erythroid cells when compared to fetal brain cells. By visualizing only the restriction fragments containing the LDB1 or CTCF transcription factor binding sites as determined by ChIP-seq (e.g. Soler et al (2010) Genes Dev; 24(3):277-89), it is possible to immediately deduce which interactions out of all the interactions involve the LDB1 complex or CTCF. It is also clear that in mouse primary erythroid cells, more LDB1 occupied restriction fragments have interactions with other positions in the locus when compared to mouse brain cells. In addition, the mean of the distance between two fragments in close proximity is larger in fetal liver cells suggesting this area of the genome is less condensed in the fetal liver when compared to fetal brain (FIGS. 3A-3D).

T2C is therefore a useful tool to detect topological domains and the different interactions within domains depending on the expression status of the genes such as the active β-globin locus in primary fetal liver cells versus the same silent locus in fetal brain. In addition, the high level of resolution of the interaction allows novel observations such as shown for the β-globin locus LDB1 binding sites and size of loops. Deletions within such a locus as for example in β-thalassemia caused by DNA deletions would be immediately visible through the change of interaction signals.

Discussion

The importance of the role of chromatin interactions in the regulation of the genes is well established. However, there is an increasing need of a quick, easy and affordable techniques to provide the information about the interactions and the compartmentalization of the genome. T2C satisfies these needs. Every restriction fragment can serve as a 'viewpoint' and all their interactions, either sort or long or to other chromosomes (not shown here), can be identified. Thus, multiple 3C-seq, 4C or 5C experiments do not have to be performed. Moreover, with T2C, the compartmentalization of the genome can be identified in the regions of interest without requiring the large sequence effort that was required for HiC, which increases the costs significantly.

Due to the design of T2C, a better coverage and resolution of the locus is obtained when compared to other techniques. The resolution of the T2C is based on the restriction enzyme used. Digesting crosslinked chromatin from primary erythroid cells and HB2 cells with HindIII or BglII resulted on an average resolution of 2.9 Kb and 6.1 Kb respectively. This provides a significantly better resolution than the usual 40 Kbp bins obtained with HiC. Moreover by adding the appropriate addresses in the oligonucleotides ligated on to the fragments (after the second cleavage before hybridisation) for sequencing purposes allows the multiplexing of different samples to the same set of oligonucleotides as the address sequence identifies the sample from which it was derived. Multiplexing further reduces the cost of T2C.

Furthermore, comparing, T2C with 3C-seq and HiC for the Igf2 locus and with previously published 3C-qPCR data for the β-globin locus, the same topological domains and interaction networks are identified. All these reveal the strengths of T2C as a tool to identify all the interactions and the compartmentalization of a specific regions of the genome.

Thus T2C is an affordable, cost effective tool to explore the local spatial organization of the genome and chromatin interactions without requiring laborious procedures or massive sequencing efforts.

Materials and Methods for Examples 1 and 2

Chromatin Isolation and Library Preparation

Nuclei from mouse primary erythroid cells from mouse fetal liver E12.5, mouse fetal brain cells and a human breast endothel cell line (HB2) were isolated and crosslinked. The chromatin was digested with a 6-cutter (HindIII for mouse cells and BglII for the HB2 cells), ligated and de-crosslinked. From the resulting libraries 50 µg DNA was digested with a frequent 4-cutter (DpnII or NlaIII for the mouse cells, NlaIII for the HB2 cells). All these steps were performed according to the 3C-seq protocol previously described (Stadhouders, R. et al. Nat Protoc 8, 509-524 (2013)).

A microarray for the β-globin locus was designed containing unique oligonucleotides as close as possible to the HindIII restriction sites spanning ~2 MB around the gene (chr7: 109875617-111971734, mm9). For the Igf2 locus, unique oligonucleotides were designed close to BglII restriction sites (ch11: 1091427-3228670, hg19) spanning an area of ~2.1 MB. The ligation products enriched by hybridization on the microarray were sequenced by paired-end sequencing yielding more than 100 million unique read pairs for the first and the second design respectively.

The final library is prepared for analysis on the Illumina Cluster Station and HiSeq 2000 Sequencer according to the Illumina TruSeq DNA protocol with modifications (www DOT illumina.com). In short, 20 µg of the digested library was purified using AMPure XP beads (Beckman Coulter) and end-repaired. The now blunt-ended fragments were A-tailed using the Klenow exo enzyme in the presence of ATP and purified again using AMPure XP beads. Indexed adapters (Illumina) were ligated to the A-tailed DNA fragments with subsequent purification using AMPure XP beads.

Array Capturing

The resulting adapter-modified DNA library was hybridized for 64 hours at 42° C. on a custom-made NimbleGen Sequence Capture 2.1M capture array according to the NimbleGen Sequence Capture array protocol (www DOT nimblegen.com/seqcapez) on the NimbleGen Hybridization System. The captured DNA fragments are eluted from the hybridised array and purified using MinElute columns (Qiagen). The captured DNA fragments are amplified by PCR using Phusion polymerase as follow: 30 s at 98° C., 24 cycles of (10 s at 98° C., 30 s at 60° C., 30 s at 72° C.), 5 min at 72° C. final extension. PCR products are purified using AMPure XP beads and eluted in 30 µl of resuspension buffer. One microliter is loaded on an Agilent Technologies 2100 Bioanalyzer using a DNA 1000 assay to determine the library concentration and to check for quality.

Cluster Generation and High Throughput Sequencing

Cluster generation is performed according to the Illumina Cluster Reagents preparation protocol (www DOT illumina.com). Briefly, 1 µl of a 10 nM TruSeq DNA library stock is denatured with NaOH, diluted to 9-10 pM and hybridized onto the flowcell. The hybridized fragments are sequentially amplified, linearized and end-blocked according to the Illumina Paired-end Sequencing user guide protocol. After hybridization of the sequencing primer, sequencing-by-synthesis is performed using the HiSeq 2000 sequencer with a 101 cycle protocol according to manufacturer's protocol. The sequenced fragments were denatured with NaOH using the HiSeq 2000 and the index-primer was hybridized onto the fragments. The index was sequenced with a 7-cycle protocol. The fragments are denatured with NaOH, sequentially amplified, linearized and end-blocked. After hybridization of the sequencing primer, sequencing-by-synthesis of the third read is performed using the HiSeq 2000 sequencer with a 101-cycle protocol.

Example 3—Determination of the 3D Structure of Genomes

The dynamic three-dimensional chromatin architecture of genomes and the obvious co-evolutionary connection to its function—the storage and expression of genetic information—is still, after ~130 years of concentrated research, one of the central issues of our time. In this example the detailed 3D architecture of the mouse and human genome can be determined directly for the first time from a few to the mega base pair level by already visual means combining a novel superior selective high-throughput high-resolution chromosomal interaction capture of all physical genomic interactions ($_{HRHT}iCIC^2$), scaling analysis, and polymer simulations: the clearly existing and differently compacted chromatin fibre is folded into loops of ~30-150 kbp which form defined loop aggregates/rosettes (sub-chromosomal domains) of ~500-1500 kbp connected by a linker. Complex (helical) loop and loop-loop architectures exist and interactions vary only to a minor but significant extent between different cell types or functional states. Beyond, scaling analysis proves shows the tight evolutionary entanglement between DNA sequence and genome architecture. Consequently, this finally opens the path to detailed architectural "sequencing" of genomes and thus true systems genomics at the limit of the "genomic uncertainty principle", all of which is of fundamental importance for genome understanding and R&D of diagnosis and treatment.

Despite the fact that the structure and function of genomes obviously co-evolved as an inseparable system to allow the physical storage and expression of genetic information, neither the dynamic three-dimensional higher-order architecture of genomes, its spatial and temporal modifications, nor its relation to functional multi-dimensional interaction and regulatory networks have yet been determined in detail since the discovery of the cell nucleus by A. van Leeuwenhoek in the 17th century and many another more recent landmark result: the discovery/description of metphase chromosomes by C. W. Nägli (1842)/W. Hofmeister (1848), the DNA by Miescher (1869), the DNA double helix by R. E. Franklin, L. C. Pauling, J. D. Watson, and F. H. Crick, (1953), the nucleosome by R. Kornberg (1973)/A. Olins & D. Olins (1974), and the 3D structure of the nucleosome by K. Luger (1997), up to sequencing of the entire human genome at the turn of the millennium. Beyond, it became apparent genome organization and function indeed build a systems genomic (Knoch, 2003) entity responsible for gene expression and thus for the intrinsic differences between individuals and their disease history as well as the receiver of functional environmental genome alterations and thus eventually external disease causes.

The size, structure, and complexity of genomes span scales from $10^{-9}$ to $10^{-5}$ m and $10^{-10}$ to $10^5$ s, and thus result in huge experimental challenges: Already how nucleosomes are spaced, positioned, remodelled, and whether/how nucleosome chains fold into fibers at physiological salt concentrations are a matters of continuing debate: e.g. Finch and Klug (1976) proposed a regular solenoid, in vivo neutron scattering experiments revealed a fiber diameter of 30±5 nm as a dominant nuclear feature, in recent contrast to no compaction at all, or to highly polymorphic and dynamic function dependent structures without which nucleosome concentration distributions, dynamic and functional properties as diffusion of macromolecules, and the scaling of the DNA sequence are unexplainable.

The higher-order chromatin architecture has been a matter of even greater debate for more than a century: Light microscopic studies by Rabl (1885) and Boveri (1909) led to hierarchical self-similar models, suggesting a territorial organization, before electron microscopy suggested a more random interphase organization—as in the models of Comings (1968, 1978) and Vogel & Schroeder (1974). In the radial-loop-scaffold model of Paulson & Laemmli (1980) chromatin loops attached to a nuclear matrix/scaffold should explain the condensation degree of metaphase chromosomes. According to Pienta & Coffey (1977, published 1984), these loops persisted in interphase, and formed stacked rosettes in metaphase. Micro-irradiation by C. Cremer & T. Cremer (1974, 1982) had already and fluorescence in situ hybridization (FISH) by C. Cremer & T. Cremer (2001), P. Lichter (1988) and publications thereafter finally confirmed a territorial organization of chromosomes, their arms, and of sub-chromosomal domains during interphase including their structural persistence during metaphase (de-)condensation (the ~-850 G, Q, R, and C ideogram bands split in 2500 sub-chromosomal domains). Whereas, chromatin rosettes were visualized by electron microscopy but not taken seriously in the western hemisphere (Erenpreisa, 1989, Belmont & Bruce (1994) proposed also based on electron microcopy the helical hierarchy chromonema fiber (CF) model, for the intra-(sub-territorial folding. Around the same time, spatial distance measurements between small FISH labeled genetic regions, led due to architecturAL "demolition" to the Random-Walk/Giant-Loop (RW/GL) model with the first analytical looped polymer description by Sachs (1995; Yokota, 1995; Yokota, 1997; Knoch, 1998; Knoch, 2002), in which 1 to 5 Mbp loops are attached to a non-protein backbone. Thereafter, a combination of distances measurements using structure preserving FISH technology, high-resolution microscopy, and huge parallel polymer simulations of chromosomes and entire cell nuclei, only could result in the rosette Multi-Loop-Subcompartment (MLS) model in which 60 to 120 kbp loops form rosettes connected by a similar linker. Again in vivo measurements of the nucleosome concentration distributions, and the dynamic and functional properties as diffusion of macromolecules are only compatible with a small loop aggregate/rosette like chromatin folding and the scaling of the DNA sequence also predicts this since otherwise the patterns found here are unexplainable otherwise.

Beyond, it became apparent, since physical interactions are at the heart of functional chemical reaction and thus process chains, that short regulatory elements containing several binding sites for transcription factors regulate gene transcription often via huge genomic separations, and thus the resulting changes in their (physical) interaction likelihood, are responsible for changes in gene expression, since either the preformed architecture or the modification or new formation of such structures, e.g. loops, is associated with spatial proximity, and thus changed interaction probability. It seems also obvious already by logical reasoning, that in the formation of these structures factors of the transcription cascades seem to play major role directly or as a dual or multiple use case as e.g. CTCF or cohesion. Consequently, both it has become apparent that genome architecture and functional regulation are responsible systems genomically via the transcription cascade for are not only responsible for the intrinsic differences between individuals and their disease history, but are in turn also the receiver of functional environmental genome alterations and thus eventually external disease cause.

To determine whether i) a locally more or less compacted chromatin fiber, ii) folded in loop aggregates/rosette exists (being consistent with all these experiments, and every a functional requirement in respect to the genomic "live" cycle from a few to the mega base pair level), iii) whether there is a general scaling behavieour of this architecture, iv) in agreement with long-range correlations of DNS sequence itself, and whether this is in agreement with v) novel in vivo measurements, a novel selective high-resolution high-throughput chromosomal interaction capture of all physical genomic interactions (everything with everything) approach was developed—$_{HRHT}\text{iCIC}^2$, which also opens the path to efficient and cheap architectural sequencing of genomes for diagnosis and treatment—in essence (see Sup. Method): i) starting with ~$10^7$ cultured/prepared cells, ii) the cells are formaldehyde fixed (i.e. DNA-DNA, RNA-RNA, DNA-RNA, protein-protein, DNA-protein, RNA-protein and more complex genomic crosslinks are formed), iii) permeablized to allow intra-nuclear restriction with a first restriction enzyme, iv) large dilution by extraction of the crosslinked fragments to allow re-ligation primarily within these complexes, before v) de-crosslinking, purification, and final shortening of the DNA chimeric fragments to sizes <500 bp by a second high-frequent restricting enzyme or by sonication (for highest resolution). Then, vi) a cleaned regional HRHTiCIC$^2$ DNA interaction fragment library is produced using DNA capture arrays (bead capturing is also possible) with ~$10^6$-$10^{10}$ molecules per unique and hybridization optimized oligo (i.e. the capture is always in the linear regime and far from saturation), which sequentially are directly placed next to the first restriction enzyme. vii) After high-throughput sequencing, the obtained sequences are trimmed to contain only a sequence piece up to the first restriction enzyme, then mapped first to the whole reference genome and in case of using two restriction enzymes also against a masked sequence containing only the regions between 1st and 2nd restriction enzyme, to use finally only 100% uniquely mapped sequences.

This novel selective $_{HRHT}\text{iCIC}^2$ approach has great advantages: i) the limiting factors compared to other interaction capture techniques now are only the sequencing capability/costs and the chosen relation between resolution of the first restriction enzyme, size of the captured region, interaction frequency range, and number of multiplexed experiments: e.g. a ~500 bp fragment resolution, in a 2 Mbp region, with a 1-$10^6$ interaction frequency range, and 10-100fold multiplexing can be easily achieved sequencing 10-100 lanes (note: also several regions can reside on one capture array). ii) Due to the design of the oligo position, the maximum of data cleanness and thus the maximum interaction information with the minimum sequencing is reached. iii) Beyond, the entire process has been optimized for structure preservation (see Sup. Methods), which is the point also during high-resolution FISH, where already slight differences have lead historically to different chromosome models. This includes also the minimization of distortions and DNA loss in each step—often achieved by a delicate/subtle laboratory/bench handling. Notably, no known structure distortion, (cost driving primers), or PCR steps are involved until sequencing here.

Beyond, with possible fragment length of down to 50-100 bp (persistence length of free DNA on average ~50 nm or ~140 bp; typical protein/nucleosome binding region ~200-500 bp) the fundamental limits of this method are not only reached, but also more importantly what is introduced here as the genomic uncertainty principle originating in the individuality of each high-resoluted interaction with a unique individual probabilistic fragment setting/condition/surrounding in each cell at a given moment in time, which is destroyed by the measurement—hence the classic definition of an uncertainty principle: i) already the cell population has a distribution of cell statuses and functional differences, ii) each fragment has a more or less dynamic (and thus stable or variable) individual DNA, RNA, protein, restriction association, thus the entire crosslinking, restriction, and re-ligation has a different individual efficiency, and, of course, iii) the DNA sequence in relation to the oligo hybridization capture, the sequencing, and mapping add also to this. Thus, in the end only probabilistic analysis and statements can be drawn as known from quantum mesoscopic systems in general and well known from the classic light double-slit experiment. Currently, there are also no means for any sensible correction, since at least currently the actual state of the influencing factors/parameters are innumerous, incalculable (especially due to their non-linearity), different for every single fragment, and besides that destroyed by the measurement. This has always been the case for any interaction capturing kind, although effects were averaged out by the low resolution (allowing for nevertheless senseless but in their effect not harmful corrections), but now the fundamental limit is reached. This opens the opportunity to perceive the interaction information integrated over all these effects in its completeness and beauty at this fundamental level with unprecedented insights.

To investigate the chromatin fiber conformation and the 3D architecture with the necessary resolution and biological impact, the human chromosome 11p 15.5-15.4, i.e. the IGF/H19 region, and the mouse chromosome 7qE3-F1, i.e. the β-globin region were selected, since both ~2.1 Mbp regions are classic well studied by FISH and 3C examples of epigenetic and local control region regulation. By using Bgl II and Hind III as first and NlaIII as second restriction enzyme this results in many fragments down to ~200-500 bp with an average of 6121 and 2915 bp, respectively. To study at even higher resolution The chromatin fiber conformation was then analysed at high resolution in general we also investigated roughly (and with low sequencing coverage) 15 regions of in total 99.5 Mbp on 10 different mouse chromosomes with ~50 to 500 bp and to an average fragment size of 549 bp. Thus, we reach molecular and nucleosomal (average nucleosomal repeat length ~200 bp, thus 3-6 kbp correspond to ~15-30 nucleosomes on average) and even subnucleosomal resolution, and thus, i.e., the level of the genomic uncertainty principle. To investigate differences between species, cell lines, and functional/architectural differences the human HB2 cell line and the cohesin cleavable TEV/HRV RAD21-eGFP cell line system (uncleaved and cleaved cohesin, Zuin et al 2013 PNAS, in press), and mouse fetal brain (β-globin inactive) and fetal liver (β-globin active) cells were used. To investigate the chromatin fibre formation also fetal liver cells were used. With ~$10^7$ input cells concerning sequencing, the corresponding material (e.g. the two different states) were multiplexed on the capture array to guarantee equal conditions. One or two lanes were sequenced either in the same sequencing run or different ones. Due to the various effects only sequences unique in the entire genome with a reasonable mismatch rate (to account for sequencing differences/errors to and in the reference genome) and cleaned for sequences only mapping between the first and second restriction sites.

Thus, sorting and plotting the regional interactions in an upright squared interaction matrix (with two mirrored triangle halves) with a logarithmic and rainbow coloured frequency range shows directly the validity of the experiments itself and the unprecedented frequency range distribution spanning 6 orders of magnitude in general and 4-5 excluding the diagonal. Thus, also rare interactions with a frequency of $10^{-4}$ to $10^{-5}$ can be visualized in this setting of region size, fragment resolution, and sequencing effort. This could easily be increased by 2-4 orders of magnitude changing this relation. Beyond, the relation of the average cumulated entries per fragment in relation to the ~$10^7$ million input cells shows an estimated ~0.1-1.0% efficiency of $_{HRHT}$iCIC$^2$. Beyond, the patterns show clearly that a level is reached where the uncertainty principle in the statistical limit reached the stable probabilistic level, since images from different sequencing lanes for the same experiment whether multiplexed or not show only minor statistical deviations.

Determination of the 3D Structure by Visual Means from T2C

All the interaction matrices of different experiments are reproducible reproducibly more or less empty, i.e. there is no prominent uniform noise or background, despite the high number of sequence reads and despite most diagonal elements showing entries of non- or self ligated fragments and thus demonstrating that a capturing oligo was present and worked. The "emptiness" is also clearly structured and not arbitrary and appears the same in replicates to an extremely high degree of detail, i.e. neither are interactions suddenly appearing statistically nor are clustered statistically somewhere near more prominent interactions. Thus, taking into account that information from definitely >$10^4$ cells survives the procedure, noise could in principle appear at any step of the procedure, and even assuming an unlikely highly biased distortion of a normal distributed noise signal towards e.g. interactions, the signal to noise ratio must be >$10^5$-$10^6$.

Even more surprising already visually the interactions themselves are even more striking in respect to the appearance of clearly distinct patterns on all scales of genomic separation and even the fact that patterns consistently are or are not reemerging on other scales (which they have to do because genomes are scale bridging systems) and also show immediately that the whole T2C procedure actually works despite of the numerous and nonlinear a parameter involved, since the chance that such patterns arise is unthinkably small. A first comparison to known viewpoints reveals agreement of T2C with e.g. 3Cseq although with much cleaner and sharper interactions for the same fragment distribution since with T2C no PCR broadening of interactions appears. Consequently, the detailed interactions patterns can be now interpreted even more easily.

Determination of the Conformation of the Chromatin Fibre by Visual Inspection:

On the smallest genomic scale, there is clearly a denser interaction pattern in the band parallel to the diagonal for genomic separations <5-10 kbp (i.e. <25-50 nucleosomes), compared to bigger genomic separations. This pattern varies independent of the local fragment resolution (which nevertheless needs to be considered) and consists of distinct interactions with noninteracting "gaps" in between, in contrast to a homogenous e.g. Gaussian like interaction "smear" decreasing for increased genomic separation. Thus, consequently visual inspection directly shows already, that on this scale—the scale of DNA/nucleosomes—stable and defined interactions exist and thus since these interactions are the outcome of spatial proximity indicate that a compaction of nucleosomes exist into an irregular but nevertheless locally defined structure, i.e. the notion of a fiber applies, which one could in general terms due its variation call "quasi-fiber" with an average density etc. Obviously, a structurally everywhere exactly identical and uniform fiber as proposed by the helical chromatin fiber model would lead in contrast to a homogenous band-like subpattern, and a constantly dynamic random walk of nucleosomes would also result in a homogenous interaction pattern with a Reighley distributed interaction decrease as function of genomic separation. Thus, by visual inspection one can readout directly the existence of a chromatin "quasi-fiber", its local interaction and thus compactness structure naturally averaged over the entire T2C procedural boundaries.

Determination of the Subchromosomal Structural Domains by Visual Inspection:

On the biggest scale the appearance of square-like domains in the range of several hundred to ~1-1.5 Mbp, with a sharp border and interacting with other domains is also immediately visible (although more prominently in the human compared to the mouse case) with several striking general properties: First the interaction frequency within the domains for the moment neglecting their substructure has in general an average uniform height and drops on the edge to another uniform height defining the interaction between subdomains. Thus, there is a staircase like behaviour of interactions in contrast to the often thought general continuous interaction decrease with growing genomic separation and a clear and defined interactions with other domains. Second at the borders of the domains there is a clear transition or linker region between domains although the interactions between domains is especially strong and complicated since near the diagonal also the chromatin quasi-fibre comes into play and since the linker is in structural terms is very flexible. Consequently, these results proof again the existence of structurally stable sub-chromosomal units, which are relatively stable and interact with each other especially well at their borders as described in the historic overview. Beyond, already on this level, the on average uniform interaction within the domain and the sharp drop at the edge very clearly indicates already towards a loop-aggregate and even rosette like structure of the domains connected by a linker, since one big loop, a random walk or fractal globule like folding all would not lead to the sharp edge and defined behaviour found here.

Determination of the conformation of the chromatin higher-order structure, i.e. the loop/aggregate/rosette folding of chromosomes by visual inspection.

On the medium scale, and thus the sub-chromosomal domain level, the interaction pattern is characterized by again clearly distinct gaps between the interactions, which are arranged in a crossed linear or grid-like pattern. Interestingly the linear pattern continuous outside the sub-chromosomal domain and "crosses" there with the linear pattern originating from the subsequent sub-chromosomal domain. Beyond, the general lower general interaction frequency level outside the domains and the less complicated interaction pattern seen there, allows to follow the linear pattern back into the domains revealing that the much simpler/clear patter outside clearly also is present within the domains, but there enriched and more complicated by additional interactions. One now can follow such a line back to the diagonal and take this as starting viewpoint following vertically to the next relevant interaction (which one can follow horizontally from outside into the domain again). Then one localizes horizontally again the interaction point on the diagonal. Repeating this gives a second interaction point on the diagonal and now one can prove that in most cases this second interaction also interacts with the first and thus starting point. Thus, by hand a grid of interactions can be constructed. This can be enhanced by projecting the interactions vertically and horizontally, resulting in a peak-like pattern along the chromosome sequence, whose peaks coincide with the crossed linear pattern. This is more prominent in the human compared to the mouse case. Since interactions on scales on tens of kilo base pairs are and can only be considered especially as chromatin looping, this means that several consecutive loops whose loop bases are visualized by the interactions have coinciding loop bases, i.e. a loop aggregate with a core, and thus also a rosette of loops with a more or less clear core. The gaps between interactions and the grid-like pattern also show that no other folding like random-walk giant loops, a chromonema like, or fractal globule pattern cannot be the origin of that since they all would result in a homogenous interaction pattern, without a clear domain border and clearly not a distinct domain border. This would also be the case for a non-compaction into a quasi-chromatin fibre, which a sea-of nucleosome organization would predict, resulting in huge and very dynamic interaction possibility. Notably, the data structure on different scales also proof also the assumption that on all scales interactions can indeed be cross-linked and depend on different underlying cross-linkable agents is correct, and thus that crosslinks between a specific DNA location or protein etc. create such patterns is very unlikely. Additionally the simple pattern is more complex due to the variation in the compaction density of chromatin and the fact that within the loops additional interactions take place of various forms: on a large scale simple loop or even super-helical like patterns seem likely, whereas on a low scale the patterns around the major loop base interactions indicate the structure of the rosette core and the local chromatin compaction and the entanglement of both there. Although the experiments at highest resolution was made to investigate the chromatin fibre conformation in more detail in general and thus involved less deep sequencing, an overall assessment of these data indeed resulted in finding several such structures which could be attributed to loop aggregates/rosettes and a detailed core structure with in and outgoing loops which leads to special interaction patterns. The interactions between the domain and their pattern can be attributed thus to two origins: On the one hand the loop aggregate/rosette cores of subsequent domains can due to the relatively low number of loops and thus density and loop dynamics interact very easily. On the other hand in a cell population there are also mitotic chromosomes where the condensation degree is naturally very high. Thus, the pattern explains both consistently the organization and its dynamics through the cell cycle and again this is only possible with a compacted chromatin fibre since otherwise, core interactions between aggregate/rosette cores would be shielded by polymer fibre exclusion.

Determination of the 3D Structure by Visual Inspection as a Function of Different Cell Types, or Treatment of the Cells, or Diseased State:

To investigate the architectural change in general as function of specie, cell type, regional, functional or structural differences due to regulation or deliberate system distortion the human IGF/H19 11p 15.5-15.4 region was investigated, and the mouse β-globin 7qE3-F1, in human HB2 and the TEV/HEV cells, and mouse fetal brain (FB) and liver (FL) cells: Whereas the general domains are clearly the same in HB2, TEV, HEV, and FB and FL cells, and thus in different cell types of the same specie, but different between human and mouse at least due to the region chosen. On a finer degree of detail human HB2 cells seem to show a more and denser interaction pattern within the domains in comparison to the TEV/HEV system. Comparing FB to FL cells does not show such an obvious difference: actually the differences a very subtle often belonging to single or a small group of interactions as can be shown for the β-globin locus where an additional loop is formed as predicted from earlier experiments. Nevertheless, the term small here is relative, since such a single loop formation actually activates the β-globin transcription, i.e. an entire pathway and thus the entire property of a cell can be changed. Beyond, cleaving cohesion (said to play a major constitutive role in genome architecture) in the TEV/HEV system leads, however, also not to dramatic changes, well actually only slightly more and more evenly spread interactions suggesting a slightly higher flexible/dynamic architecture but not as big as previously thought as in a genome wide analysis. Thus, cohesion cannot be single and definitely not major/singe component responsible agent, but instead is one of obviously several components influencing/forming genomic architectures and shows the evolutionary balance between flexibility and stability of genome architecture. Consequently, these variations show not only the reproducible quality of T2C and its analysis under different conditions and that a clear general genome architecture exists, but also that a the reached level of the genomic uncertainty principle in essence locally every detail is a variation of the great theme to be considered to fine-regulate the system. Thus, obviously in only ~2 Mbp big genomic regions a wealth of interaction data is present to be carefully analysed in detail.

Determination of 3D Chromatin Higher Order Structure by Monte-Carlo and Brownian-Dynamics Simulations in Comparison to T2C To explore and understand this behaviour on all scales independently and in a clearer manner with preset conditions recently polymer models have been developed to evaluate (not to fit) in general experimental results, designs and hypotheses about the three-dimensional genome organization. There the resolution is based on stretchable, bendable polymer segments, and volume exclusion with a resolution comparable to ~1-2.5 kbp and featuring the Random-Walk/Giant-Loop model in which large loops (0.5-5.0 Mbp) are linked by a linker resembling a flexible backbone, and featuring the Multi-Loop Subcompartment (MLS) model with rosette-like aggregates (0.5-2 Mbp) with smaller loops (60-250 kbp) connected by linkers of variable sizes (60-250 kbp). These simulations were enhanced and for the first time two-dimensional spatial distance and interactions maps (for different crosslink probabilities and extent) were calculated with extremely high statistical validity. Visual comparison reveals immediately, that all above described effects interpretations are in agreement with the simulations, and beyond the interactions are a function of all model parameters even in slight details considering that no nucleosomes where modelled here: i) in general the interaction degree depends on the interaction and crosslink probability, ii) the domain size, domain separation, and spacing of loops are proportional to their size, iii) the interactions between the domains depend on the linker size, the size and number of loops, i.e. density of the rosettes. Thus, the subtle combination of density of rosettes due to loop size, loop number, chromatin fibre persistence and the thus resulting exclusion effects leading eventually for high numbers to spread out and shielding effects of rosettes, as well as the subtle influence on the interaction pattern between entire domains. The linker between domains and its proportionality to inter-domain interactions is as clearly visible as well as non equilibration effects which we deliberately show here to create an understanding of the interactions of loops at aggregate/rosette borders and similar effects. Also the in general large emptiness of interaction matrices and the link to the existence of a dedicated chromatin fibre is obvious and also proves that the crosslink probability, radius, and frequency can be estimated to be relatively low although since the relation contains a too complex parameter set not unambiguously fittable. The models show also clearly the special behaviour at the loops bases of the rosettes, which in reality due to the variation of the compaction in reality might be more complex, although experiments with highest resolution show, that various such structures exist but have to be investigated in much further detail in the future.

Determination of 3D chromatin higher-order structure by determination of the scaling behaviour of T2C from the scaling behaviour of the frequency of interactions as a function of the genetic distance between interactions and in comparison to the scaling behaviour of Monte-Carlo and Brownian-Dynamics simulations and the scaling of the long-range correlations in the DNA itself:

To investigate in a unified scale-bridging manner the behaviour from scales of several base pairs, via the mega base pair and subdomain level, up to the scale of entire chromosomes and thus nucleus (spanning scales from $10^{-9}$ to $10^{-5}$ m), we introduced scaling analysis and showed its capabilities: The scaling of the interaction frequency as function of the genomic separation the different simulated models given by shows clearly long-range scaling, with a multi-scaling behaviour with a fine-structure attributable to i) the general interaction decrease, i.e. spatial distance increase, ii) the sub-chromosomal domain like structure, iii) the aggregated loop/rosette like structure in the subdomains. All parameter variations can be re-found in a changed scaling behaviour on scales here. This is in agreement, with other measures of scaling. Thus, there is no uniform scaling as e.g. seen in self-similar fractals bridging and the same on all scales, but its deviation shows the substructure in domains and loops.

The scaling behaviour of the different regions is in comparison a scaling behaviour of subset of a chromosome and thus is dominated by the local architecture deviations from the general scaling behaviour and is also compromised by the amount of interactions used here. Nevertheless, the scaling behaviour shows i) a long-range multi-scaling behaviour with a fine-structure, ii) with subtle but not in general differences for the various specie, cell type, functional/distortion differences.

The scaling behaviour of interaction frequencies as function of their genomic separation of different published experiments on the entire genome shows also i) a long-range multi-scaling behaviour with a fine-structure, ii) with subtle but not in general differences for the various specie, cell type, functional/distortion differences. Both experimental and modelled scaling behaviours, however, only agree with loop aggregated/rosette like genome architectures with loop aggregates (0.5-2 Mbp) with smaller loops (60-250 kbp) connected by linkers of variable sizes (60-250 kbp).

Since what is near in physical space should also be near in DNA sequence space, since mutations of all sorts will be biased by genome architecture itself, we also investigated the correlation behaviour of the DNA sequence by the most simple correlation analysis possible, i.e. the mean square deviation of the base pair composition within windows of different size for two different human and mouse entirely sequenced strains: i) long-range power-law correlations were found using correlation analysis on almost the entire observable scale, ii) with the local correlation coefficients showing a species specific multi-scaling behaviour with close to random correlations on the scale of a few base pairs, a first maximum from 40 to 3400 bp, and a second maximum from $10^5$ to $3 \times 10^5$ bp, and iii) an additional fine-structure is present in the first and second maximum. The behaviour in general and in detail is stronger in the human compared to the mouse case, but within the different chromosomes nearly identical and only deviating for certain chromosomes to a somewhat larger extent. The behaviour on all scales is not only equivalent to the long-range multi-scaling of the genome architecture in detail but also at the right scales. Thus, the second maximum found corresponds to in size and position to the sub-chromosomal domains. Especially on the fine structural level, the previously already proven association to nucleosomal binding at the first general maximum can now be extended to second maximum as well and associated with the looped structure in there as previously predicted.

Beyond, the interaction scaling at highest resolution shows the same behaviour across different chromosomes as the scaling behaviour of the DNA sequence in the same maximum: although a fine-structure cannot be found due to the experimental resolution, the general behaviour with a broad peak and a stronger interaction decrease on scales above ~4 kbp strongly suggests, in both the interaction experiment and in the DNA sequence, that a compacted chromatin fibre indeed exists.

Methods for Example 3 with a Detailed Description of T2C:

HB2 Cell Line and Cell Culture

HB2 cells (1-7HB2, a clonal derivative of the human mammary luminal epithelial cell line MTSV1-7) were cultured in DMEM supplemented with 0.2 mM L-glutamine, 100 units/ml penicillin, 100 mg/ml streptomycin, 10% FCS, 5 μg/ml hydroxycortisone, and 10 μg/ml human insulin. In a previous 3C study we confirmed the karyotype and the DNA methylation of several regions.

TEV/HRV Cell Line System and Cell Culture

The cleavable TEV/HRV RAD21-eGFP cell line system is a HEK293T cell line system, which was transfected with a pRTS-1 vector encoding for a cleavable RAD21-eGFP fusion protein and an siRNA for endogenous RAD21 knock-down. Both are expressed by doxycycline induced activation of a bidirectional promoter in between and thus simultaneously. For the RAD2-eGFP fusion-protein, a cleavable RAD21, where the first RAD21-separase cleavage site is replaced by that of the 3C protease of the human rhinovirus (HRV protease) using a PCR-based mutagenesis (the second cleavage site remained unchanged to ensure less cell cytotoxicity) was inserted before eGFP. The tobacco etch virus protease (TEV protease), does not recognize the HRV cleavage site and thus can act as a control. The endogenous RAD21 knock-down sequence allows knock-down with the following 3'UTR-directed siRNA's:

```
                                          (SEQ ID NO: 1)
        5'-ACUCAGACUUCAGUGUAUA-3'  (Sccl-1), (SEQ ID NO: 2)
        5'-AGGACAGACUGAUGGGAAA-3'  (Sccl-2).
```

For generation of the TEV/HRV RAD21-eGFP cell line system the original HEK293T cell line was cultured in DMEM supplemented with 0.2 mM L-glutamine, 100 units/ml penicillin, 100 mg/ml streptomycin, 10% FCS, and was grown at 37° C. and 5% $CO_2$. For the transfection Lipofectamine 2000 (Invitrogen) according to the instructions of the manufacturer was used. Cells carrying the vector were selected by growth in 150 μg/mL hygromycin containing medium. Single clones were picked and analysed for expression of RAD21cv and RAD21 wt constructs and depletion of the endogenous RAD21 three days after induction with 2 μg/ml doxycycline. The resulting TEV/HRV RAD21-eGFP cell line was as well cultured in DMEM supplemented with 0.2 mM L-glutamine at 37° C. and 5% $CO_2$.

For experiments and to activate transgene expression with HRV (or TEV which serves as a control, thus a transfection takes place, but no cleavage) the cells were cultured for 3 days in the presence of 2 μg/ml of doxycycline. Thereafter, cells were split, reseeded until 50% confluency and transfected with HRV or TEV vectors using Lipofectamine 2000 (Invitrogen) again according to the instructions of the manufacturer. 24 hours after protease transfection the cells were used for the experiment.

Cell Preparation from Mice

For mouse fetal liver and fetal brain cells, ~10 embryos on day 12.5 of pregnancy from one to two transgenic FVB/N mice were used for the ~10 million cells required by the experiment to have a complex enough cell population and enough DNA in the end to be sequenced: The mice were cleaned with 70% EtOH and the abdomen was opened to remove the cervix containing the embryos, before cutting them lose and removing them from the yolk sac and placenta. Small and underdeveloped embryos were discarded. The embryos are collected in petri dishes on ice with 0.5 ml 10% FCS/PBS. Then the fetal liver and brain were dissected from the embryos and collected in tubes (1 ml) on ice containing again 500 μl 10% FCS/PBS. The cells were then resuspended with a P1000/1 ml plastic pipette tip and connective tissue was digested by adding 25 □l of a 2.5% Collagenase stock (0.125% end concentration) and incubated for ~45 min at 37° C. Thereafter, the cell suspension was transferred to falcon tubes with 12 ml 10% FCS/PBS at room temperature and thereafter was gently squeezed through a scraper mesh which was placed inside a 6-well plate using again a P1000/1 ml plastic pipette tip. The mesh was washed with 2 ml 10% FCS/PBS at room temperature to get all the cells from the mesh. The resulting single cell suspension was again collected in falcon tubes with an end volume of 12 ml 10% FCS/PBS at room temperature. Notably, we tried to keep the stress of the cells to the minimum, to avoid any damage to the cell nuclei. Both after the resuspension, the Collagenase treatment, and/or after the scraping of fetal liver and brain material/cells were spotted on glass slides to check for cellular and especially nuclear integrity by microscopy, with or without staining of the nucleus with DAPI (or eventually any other immunofluorescence or fluorescence in situ hybridization).

$_{HRHT}$iCIC$^2$ Crosslinking/Fixation of Cells

For crosslinking/fixation of the genome and the entire cells, the cells were first counted and their concentration adjusted to 10 million in 12 ml 10% FCS/PBS at room temperature and put into 15 ml polypropylene tubes (used for cell culture and thus not excessively absorbing/fixing cells to the tube wall, Greiner Bio One). Then 650 µl of a 37% formaldehyde PBS solution were added, i.e. a final concentration of 1.9% of formaldehyde is used for crosslinking/fixation, at room temperature for 10 min while softly tumbling to avoid cell aggregation. Note: the concentration of formaldehyde for crosslinking/fixation at this stage is ideal for the following steps and in respect to cell/nuclear integrity for the human and mouse cells we used here; although this might hold in general, cases are known where other concentrations and incubation times achieve better results. Thus, the tube was put on ice (from now on we kept everything on ice up to the 1 st restriction of the DNA (see below) to avoid any damage of the material) and 1.6 ml of cold 1M Glycine in PBS were added to stop the crosslink/ fixation reaction. Thereafter, the cells were spun down for 8 min at 1300 rpm at 4° C., the resulting pellet was washed in ice-cold PBS, and taken up first in 1 ml before adding up to 14 ml of PBS, followed again by spinning down for 8 min at 1300 rpm at 4° C. After discarding the supernatant, the pellet could now also be frozen for storage, although we advise to straight away continue with lysis and the 1st restriction. Again cells were spotted on glass slides to check for cellular and especially nuclear integrity by microscopy, with/without staining of the nucleus with DAPI (Note: again the cells could now also be used eventually for any other immunofluorescence or fluorescence in situ hybridization experiment).

Preparation of Cell Nuclei and 1st Nuclear Genomic DNA Restriction

For lysis of the cells and to prepare cell nuclei, we prepared always 5 ml of a fresh (for full activity) lysis buffer on ice (!) consisting of 10 mM Tris pH 8.0 (50 µl 1M), 10 mM NaCl (10 µl 5M), 0.2% NP-40 (100 µl 10%), 100 µl 50× complete prot. Inhib. (50×=1 tablet in 1 ml PBS), and filled up with up to 5 ml MilliQ (4.74 ml). The pellet prepared in the last step of crosslinking/fixation was taken up in 1 ml of this lysis buffer, resuspended and filled up with another 4 ml to a total of 5 ml and incubated for 10 min on ice. The now free cell nuclei were spun down for 5 min at 1800 rpm at 4° C., the pellet was taken up in 0.5 ml of ice cold PBS safe-lock tube, and spun for 1 min at 2600 rpm a at 4° C. Again here it is possible after removal of the supernatant and snap-freezing to store the nuclei at −80° C. For a check we always spotted nuclei on glass slides to check for nuclear integrity by microscopy and/or staining of the nucleus with DAPI.

For the 1st restriction the nuclei were now resuspended in 0.5 ml/tubes with 1.2× restriction buffer (60 µl restriction buffer, 440 µl MilliQ and adjusted for BSA if necessary) and transferred to a 1.5 ml safe-lock tube. Then to gently permeabilize the nuclear lamina the tubes were put to 37° C. and 7.5 µl of 20% SDS (0.3% endconcentration) were added, and incubated at 37° C. for 1 h, while shaking at 900 rpm. After adding 50 µl of Triton-X-100 (2% endconcentration) for further gentle permeabilzing the nuclear lamina, the nuclei were again incubated at 37° C. for 1 h, while shaking at 900 rpm. Note: both the SDS and Triton-X-100 step need to be carried out with great care to avoid any decrosslinking—again we checked that by checking the nuclei microscopically with and/or without DAPI staining. For future controls of the undigested material (the so called 1st unrestricted control) now a 5 µl aliquot was taken and stored at −20° C. Then 400 Units of the selected restriction enzyme was added and incubated over night (~20 h) at 37° C. For the human cells in all cases the restriction enzyme BglII (Roche) was used. For the mouse cells we used either HindIII (Roche) or ApoI (New England Biolabs) was used. Note: even though its optimal temperature is 50° C. for ApoI 37° C. should be used to prevent partial decrosslinking of the sample ;-). And again for future controls of the restriction now a 5 µl aliquot was taken and stored at −20° C. (the so called 1st restricted control). After the 1st restriction 40 µl of 20% SDS (enconcentration 1.6%) was added to the remaining sample to stop the restriction and for further breakdown of the nuclear lamina by incubation at 65° C. for 20-25 min, while being shaken at 900 rpm.

Dilution, Re-Ligation and De-Crosslinking of Restricted Genomic DNA

Thereafter, the fully digested nuclear material was diluted by transferal to a 50 ml falcon tube and addition of 6.125 ml 1.15× ligation buffer (6.125 ml: 5421 ml MilliQ+704 µl ligation buffer). Then 375 µl of 20% Triton-X-100 (endconcentration 1.0%) was added and incubated in a 37° C. water bath for 1 h, while being shaken every 10 min by hand. Then 20 µl Ligase HC 5 U/µl (100 U in total, Roche) was added and incubated at 16° C. over night (~20 h) followed by an additional 30 min of incubation at room temperature. To de-crosslink the non-ligated and ligated DNA 30 µl 10 mg/ml Proteinase K was added and incubated at 65° C. in a water bath over night (~20 h). Again for future controls of the relegation and de-crosslinking now a 5 µl aliquot was taken and stored at −20° C. (so called re-ligation/de-crosslink control).

DNA Purification and 2nd (Re-Ligated-)DNA Restriction/ Sonication

For further treatment of the sample, first the DNA was purified by adding 30 µl 10 mg/ml RNAse (300 µg in total) and incubation for at 37° C. for 30-45 min, followed by brief cooling to room temperature and addition of 7 ml phenolchloroform and vigorous shaking. Then the sample was centrifuged at 4,000 rmp (2200×g) for 15 min, before the upper phase was put in a new 50 ml tube and 7 ml of MilliQ was added as well as 1 µl of glycogen per ml, 1.5 ml of 2M Sodium Acetate pH 5.6, and add 35 ml of 100% ethanol to enhance the purification, gently but thoroughly mixed and thereafter put at −80° C. for 1.5-3 h. This was followed by direct centrifugation at 4,000 rmp (2200×g) for 15 min, supernatant removal, addition of 10 ml of 70% EtOH, resuspension, and again centrifugation at 4,000 rmp (2200× g) at 4° C. for 15 min. After supernatant removal, the pellet was dried for 20 min and was dissoluted in 150 µl of 10 mM Tris pH 7.5 at 37° C. for 30 min. Again for future controls of the relegation and de-crosslinking now a 5 µl aliquot was taken and stored at −20° C. (so called 1st purification control).

Thereafter, the resulting re-ligated and de-crosslinked purified material was shortened by a 2nd restriction: First, to control the amount of DNA at this stage an aliquot of 1 µl was run alongside a reference sample of species-matched genomic DNA of known concentration on a 2% agarose gel. Then the DNA was adjusted in 0.5 ml/tubes to a 100 ng/µl concentration and restricted with the 2nd restriction enzyme by adding 1 U per µg of DNA of the selected restriction enzyme and incubated over night (~20 h) at 37° C. For the human cells in all cases the restriction enzyme NlaII (New England Biolabs) was used. For the mouse cells we used either if HindIII was used as 1st restriction enzyme DpnII (New England Biolabs) or if ApoI was used as 1st restriction enzyme sonication with 10 cycles of 15 sec on and 45 sec off.

Treatment of the Various DNA Controls

For controls of the integrity of the DNA at the different stages the following controls were used: i) 1st unrestricted control, ii) 1st restricted control, iii) re-ligation/de-crosslink control, iv) 1st purification control, and v) 2nd restriction/final purification control. These samples were controlled on a 2% agarose gel with corresponding plasmid DNA, which was restricted alongside, re-ligated and purified as external restriction control. For controls i)-iii) the aliquots were incubated with 10 µl Proteinase K (10 mg/ml) in 90 µl 10 mM Tris pH 7.5 at 65° C. for at least 1 h. The DNA was purified by adding 3 µl 10 mg/ml RNAse and incubation for at 37° C. for 30-45 min, followed by brief cooling to room temperature and addition of MilliQ up to 500 µl (~400 ml) as well as 500 µl phenol-chloroform and vigorous shaking. Then the controls were centrifuged at 13,200 rmp for 15 min, 2 µl of glycogen per ml, 50 µl of 2M Sodium Acetate pH 5.6, and add 850 µl of 100% EtOH were added, gently but thoroughly mixed and snap-frozen before direct procession to centrifugation at 13,200 rmp for 20 min, followed by supernatant removal, addition of 1 ml 70 EtOH, centrifugation at 13,200 rpm at 4° C., renewed supernatant removal, pellet drying for 20 min and dissolution in 20 µl of 10 mM Tris pH 7.5 at 37° C. for 30 min.

$_{T2C}$General DNA Whole Genome Sequencing Library Preparation

In general the DNA T2C fragment library was prepared for sequencing analysis on the Illumina Cluster Station and HiSeq 2000 Sequencer according to the Illumina TruSeq DNA protocol with enhancing modifications from us (www DOT illumina.com, TruSeq DNA sample prep LS protocol; part #15026489 Rev. C): i) purification of the DNA fragments, ii) end-repair to reach blunt end status, iii) 3'-end Adenylation to avoid chimera, in the iv) sequencing adapter ligation including eventual multiplexing step, and finally v) purification of the T2C whole genome sequencing DNA fragment library.

Therefore, first the concentration of the T2C DNA fragment library was measured again for fine tuning using 1 µl of material using Quant-it dsDNA broad range assay kit. Then the samples were split into 4 sets of 5 µg each of the T2C DNA fragment library and the following complete procedure done for each of these 4 sets of material:

i) To purify the T2C DNA library after the 2nd restriction AMPure XP beads (Beckman Coulter) were used by adding 1.8 µl AMPure XP beads per 1.0 µl of digested DNA. This was incubated at room temperature for 5 minutes, placed on the magnetic stand and incubated at room temperature for 5 minutes, and the supernatant was discarded without disturbing the beads. The beads were washed 2 times with freshly prepared 70% ethanol, placed at 37° C. for 5 minutes to let the beads dry. Then the beads were resuspended in 50 µl PCR grade water and incubated at room temperature for 5 minutes, placed on the magnetic stand for 5 minutes, and finally 50 µl supernatant was transferred to a new tube. One microliter was finally loaded on an Agilent Technologies 2100 Bioanalyzer using a DNA 1000 assay to determine the quality of the purified digested DNA.

ii) For end-repair of the T2C library DNA fragments, since they were restricted or sonicated before with overhanging ends, 4 material sets were each in 50 µl transferred to a 96 well plate. Since no in-line control reagent to avoid contamination of the material was used, 10 µl of resuspension buffer were added, followed by 40 µl of end repair mix, and mixed thoroughly but gently pipetting the entire volume up and down 10 times. Then the plate was covered with a micro-seal 'B' adhesive seal and placed on the pre-heated thermal cycler at 30° C. for 30 min. After removing the adhesive seal from the plate, first the AMPure XP beads were vortexed until they were well dispersed, and 160 µl (consisting of 136 µl of AMPure XP beads mixed with 24 µl of PCR grade water) were added to the wells and the entire volume was again pipetted thoroughly but gently up and down 10 times. After 15 min of incubation, the plate was put on the magnetic stand at room temperature for another 15 min until the liquid appeared clear. Then twice 127.5 µl of the supernatant was removed, and thereafter 200 µl of freshly prepared 80% EtOH was filled into the well of the plate without disturbing the beads, incubated at room temperature for 30 sec and discarded again without disturbing the beads. This was repeated twice before drying of the plate for 15 min. Only thereafter the plate was removed from the magnetic stand and the pellets resuspended with 17.5 µl of resuspension buffer, followed by 10 times thorough but gentle mixing by pipetting 10 times up and down. After incubation at room temperature for 2 min, the plate was put back on the magnetic stand at room temperature for 5 min again until the liquid appeared clear, and then 15 µl of the clear supernatant was removed containing the end-repaired material ready for the Adenylation of the 3'-ends in the next step.

iii) For 3'-end Adenylation of the end-repaired $_{HRHT}$iCIC DNA fragment libraries, i.e. to prevent the blunt ends from ligating to one another, and thus to ensure a low rate of chimera (concatenated template) formation during the adapter ligation reaction in step iv), Klenow exo enzyme in the presence of ATP was used. A corresponding single 'T' nucleotide on the 3' end of the adapter provided a complementary overhang for ligating the adapter to the fragment.

Therefore, 15 µl of the end-repaired T2C DNA fragment library were transferred to a new 0.3 ml PCR plate. Since the in-line control reagent to avoid contamination of the material was again not used 2.5 µl of the resuspension buffer was added, followed by 12.5 µl of thawed A-tailing mix, pipetted thoroughly but gently up and down 10 times. Then the plate was sealed with a microseal B' adhesive seal, and the plate was placed on a pre-heated thermal cycler at 37° C. for 30 min. Immediately after removal of the plate from the thermal cycler, the adapter ligation took place.

iv) To ligate the sequencing adaptors using the Illumina provided indexed adapters #6 and #12, DNA adapter tubes and stop ligation buffer tubes were used, and centrifuged to 600×g for 5 seconds. Immediately before use, the ligation mix containing tube was removed from the −25° C. storage as recommended by Illumina. Since the in-line control reagent to avoid contamination of the material was again not used 2.5 µl of the resuspension buffer was added to the wells of another FOR plate, and 2.5 µl of the ligation mix was added as well. Then 2.5 µl from the appropriate adaptor tubes was added and thoroughly but gently pipetted up and down 10 times. Then the plate was sealed again with a microseal B' adhesive seal and the plate centrifuged to 280×g for 1 min. Thereafter, the plate was incubated on a pre-heated thermal cycler at 30° C. for 10 min, the plate was taken down from the cycler, the adhesive seal removed, 5 µl of the stop ligation buffer was added, and thoroughly but gently pipetted up and down 10 times.

v) To purify the sequencer adapted T2C DNA fragment libraries again AMPure XP beads were used. Therefore, AMPure XP Beads were centrifuged until they were well dispersed and 42.5 µl of mixed AMPure XP Beads were added to the wells and thoroughly but gently pipetted up and down 10 times, before incubation at room temperature for 15 min. Then the plate was placed on the magnetic stand at room temperature for minimum 5 min or longer until the liquid appeared dear. Then 80 µl of the supernatant were removed from each well of the plate and while the plate remained on the magnetic stand, 200 µl of freshly prepared 80% EtOH were added without disturbing the beads, and incubated at room temperature for 30 sec. The complete supernatant was then removed. This EtOH wash was done twice, before the still on the magnetic stand resting plate was air-dried at room temperature for 15 min. After removal from the magnetic stand, the dried pellet was resuspended using 52.5 µl of resuspension buffer, and thoroughly but gently pipetted up and down 10 times. After incubation for 2 min, the plate was put back to the magnetic stand at room temperature for minimum 5 min or longer until the liquid appeared clear. Then 50 µl of the clear supernatant was transferred to a new 0.3. PCR plate for a second cleanup, and 50 µl of vortexed AMPure XP beads added, and thoroughly but gently pipetted up and down 10 times. Then the plate was again incubated at room temperature for 15 min, the plate was placed again on the magnetic stand at room temperature for minimum 5 min or longer until the liquid appeared clear. 95 µl of the supernatant were removed, while the plate still remained on the magnetic stand, 200 µl of freshly prepared 80% EtOH was added to each well without disturbing the beads, incubated at room temperature for 30 sec. The complete supernatant was then removed. This EtOH wash was done again twice, before the still on the magnetic stand resting plate was air-dried at room temperature for 15 min. After removal from the magnetic stand, the dried pellet was resuspended using 22.5 µl of resuspension buffer, and thoroughly but gently pipetted up and down 10 times. Again after incubation for 2 min the plate was put back to the magnetic stand at room temperature for minimum 5 min or longer until the liquid appeared clear. Finally 20 µl of the clear supernatant from each well of the plate were collected and the material from each of the 4 in parallel treated T2C DNA fragment libraries splits pooled.

Regional DNA Sequencing Capture Microarray Design

To achieve a high-resolution and allow for high-throughput multiplexed sequencing and thus to achieve a highly relevant local interaction mapping, i.e. to achieve a high quality T2C$^2$, special capture arrays were designed to select specifically for genome regions of interest avoiding sequencing of unnecessary background, i.e. to create a regional DNA sequencing library optimized for selection of the re-ligated DNA pieces after the 1st restriction, i.e. directly for interactions only in specific and relatively small genomic regions. Therefore, in a close cooperation with NimbleGen, we designed DNA oligos for 2.1 M capture microarrays, i.e. capture microarrays capable of in principle fishing 2.1 million different genomic sequences with the same amount of different oligos. To achieve a real high quality result T2C only (!) one oligo was placed up- and one downstream as near as possible to the 1st restriction site used in the nuclear whole genome restriction, since the interest lies in sequencing just each side after re-ligation of this 1st restriction. The oligos were designed by NimbleGen and us for the selected regions of the human and mouse genomes using genome builts mm9 and HG19 with oligo length of 72±3 bp, unique appearance (no mismatch allowed) in the entire genome, and with respect to best and similar, i.e. similar hybridization, capturing on a microarray. Then the oligos were further selected: in the case of using a 2nd restriction enzyme to shorten the re-ligated DNA library for sequencing the oligo had to be situated between the 1st and 2nd restriction site. In the case of using sonication to shorten the re-ligated DNA only oligos within 150 bp of the 1st restriction site were chosen. If only one oligo was present, which crossed either the 1st or 2nd or even both restriction sites, only cuts at the oligo beginning or end of in total not more than 10% were allowed, i.e. that the oligos could definitely capture DNA pieces with a minimum of 62 bp to guaranty specificity and similar hybridization efficiency. The same condition was applied in the sonication case, for the 1st restriction side. Thereafter, we mapped the oligos on the genome and controlled by hand whether the conditions were fulfilled and whether the oligos were properly placed in respect to other genome features. For production of the microarray the number of the 2.1 million possible different oligos $O_{array}$ was divided by the number of selected $O_{selected}$ and then each selected oligo spotted $N_{spotted}$ times, with $N_{spotted}$ $$\text{Abs}\left(\frac{O_{array}}{O_{selected}}\right),$$

on the actual capturing array during the production process of the capturing microarray by NimbleGen. Thus, with the number of oligos used for capturing (see below) using a 1st and 2nd restriction enzyme we can be sure to have ~$10^{10}$ oligo molecules for each different oligo on the microarray, and thus with the $10^7$ cells we use as input, we are far away from saturation of the array by a factor of >$10^5$ to $10^6$. In the case of the experiment using sonication with ~250 times more oligos and in total ~50 times more genomic regions covered that is still >$10^2$, if considering the losses in the experimental procedures up to the capture array.

Concerning the experiments using a 1st and 2nd restriction enzyme, the balance between the region size chosen, the resulting size of the interaction matrix, i.e. the all possible interactions between all restriction fragments within this region, and the sequencing capabilities to achieve a high frequency range of a minimum of 4 to 5 orders of magnitude for each possible interaction (we assume an average of 2 to 3 orders of magnitude, which results in a spread of 4 to 5 orders of magnitude) was calculated. Thus, for a sequencing capability in two sequencing lanes of ~300 and 500 million sequences, i.e. 300 and 500 million sequencings of possible interaction events, with the aim of achieving on average of 100 to 1,000 sequencing events per interaction 500 to 1,000 oligos and thus interaction fragments are optimal. The genomic region then covered depends only on the resolution, i.e. average spacing of the 1st restriction enzyme within the genome.

In the case of a 1st and 2nd restriction enzyme we chose the oligos and capture arrays as follows: In the human case this was done for the H19/IGF2 region on chromosome 11 from basepair position ~1,110,650 to ~3,216,350, i.e. a 2,105,700 bp sized region and 525 oligos. In the mouse case this was done for the β-Globin region on chromosome 7 from basepair position ~109,876,350 to 111,966,600, i.e. a 2,090,250 bp sized region and 800 oligos.

$_{HRHT}$iCIC$^2$ Regional DNA Sequencing Library Preparation—Microarray Capturing To produce a subselected regional T2C DNA fragment sequencing library from the T2C whole genome DNA fragment sequencing library, the pooled DNA library after ligation of the sequencing adapters was subject to subselection with the above described newly and specifically developed capturing microarrays using the NimbleGen Array capture protocol and hybridization system with enhancing modifications from (www DOT nimblegen.com/seqcapez, NimbleGen Arrays User's Guide, Sequence Capture Array Delivery version 3.2): The entire procedure consisted of i) microarray hybridization, ii) washing before iii) elution of the captured regional DNA library from the microarray.

i) Therefore, 3 h before the capturing, the hybridization system was set to 42° C., a first heat block was set to 95° C., and another one to 70° C., to equilibrate. Then the hybridization mixture was prepaired by adding 300 µl of 1 mg/ml Cot-1 DNA to the pooled DNA library after ligation of the sequencing adapters. In the case of using multiplexed samples not only the 4 sets of material were pooled but also the multiplexed samples were pooled. This saves microarray capacity and since the amount of DNA to be captures is war of the saturation of the microarray this leaves room for multiplexing up to 10 to 100 samples depending on the DNA amount, concentrations, and method to be used. Here multiplexing was only down by pooling 2 different materials. Then the sample was dried in a SpeedVac at 60° C. for around 30 to 45 min, 11.2 µl of VWR water was added for rehydration, vortexed and centrifuged at maximum speed for 30 sec, before placement on the 70° C. heat block for 10 min to fully solubilize the DNA. After a second vortexing and again centrifugation at maximum speed for 30 sec, 18.5 µl of 2×SC hybridization buffer and SC hybridization component A are added, followed again by vortexing and again centrifugation at maximum speed for 30 sec. Then to denature the DNA the sample was placed on the 95° C. heat block for 10 min before another centrifugation at maximum speed for 30 sec. Thereafter, the sample was placed at 42° C. and from there immediately loaded on the microarray hybridization chamber (the complete microarray system was prepared in parallel) and hybridized at 42° C. for 64 h.

ii) To wash the captured regional T2C DNA library on the microarray first the elution chamber was assembled according to the NimbleGen array user guide. Therefore, the microarray slide was removed from the 42° C. NimbleGene hybridization system and placed directly into the disassembly basin containing 100 ml of SC wash buffer II heated to 47.5° C. After ~10 sec used for equilibration the mixer was peeled of and the slide was transferred to a second wash tube containing SC wash buffer II at 47.5° C., the closed wash tube was inverted 10 times at a rate of 1 inversion per second. Then the slide was transferred to a new wash tube containing 32 ml of stringent wash buffer at 47.5° C., and the closed tube was inverted 10 times at a rate of 1 inversion per second, before resting at 47.5° C. for 5 min, and again inverted 10 times at a rate of 1 inversion per second. Then the slide was again transferred to a new tube containing 32 ml of stringent wash buffer at 47.5° C., and the closed tube was inverted 10 times at a rate of 1 inversion per second, before resting at 47.5° C. for 5 min, and again inverted 10 times at a rate of 1 inversion per second. Then the slide was again transferred to a new tube containing 32 ml of SC wash buffer I at room temperature, and the closed tube was inverted at a rate of 1 inversion per second for 2 min. Then the slide was again transferred to a new tube containing 32 ml of SC wash buffer II at room temperature, and the closed tube was inverted at a rate of 1 inversion per second for 1 min. Then the slide was again transferred to a new tube containing 32 ml of SC wash buffer III at room temperature, and the closed tube was inverted 10 times at a rate of 1 inversion per second.

iii) To elute the captured regional T2C DNA fragment sequencing library from the microarray the slide was transferred to the NimbleGen ED elution system at room temperature. Then ~900 µl of 125 mM NaOH were added to the elution chamber until it is full, and incubated for 10 min. The eluted regional DNA fragment sequencing library was pipetted to a 1.5 ml tube and filled up to 900 µl of 125 mM NaOH, followed by division equally in two new tubes containing 516 µl of a well mixed solution of 16 µl 20% acetic acid solution and 500 µl Qiagen Buffer PBI prepared beforehand in a 1.5 ml tube. Then the mixture was transferred to a single MinElute column on a centrifuge to draw the solution through the column in several steps of 700 µl each. Then 750 µl buffer PE was put the column and centrifuged through. Then the MinElute column was put into a 2 ml collection tube and centrifuged at maximum speed for 1 min. to remove any residual buffer PE. The flow-through was discarded, before placement of the MinElute column in a clean 1.5 ml tube, 25 µl of buffer EB was added to the column, incubated for 1 min, and centrifuge at maximum speed for 1 min.

T2C Amplification, Cluster Generation, and Paired-End High-Throughput Sequencing First for paired-end sequencing the T2C regional DNA fragment sequencing library was enriched for sequencing first by PCR using Phusion polymerase using 30 sec at 98° C., 12 cycles of (10 sec at 98° C., 30 sec at 60° C., 30 sec at 72° C.), 5 min at 72C final extension. For each 1 µg of T2C regional DNA fragment library 5 µl of the PCR primer cocktail and 25 µl PCR master mix was added to the PCR plate. For purification AMPure XP beads (Beckman Coulter) were used by adding 1.8 µl AMPure XP beads per 1.0 µl of DNA. This was incubated at room temperature for 5 minutes, placed on the magnetic stand and incubated at room temperature for 5 minutes, and the supernatant was discarded without disturbing the beads. The beads were washed 2 times with freshly prepared 70% ethanol, placed at 37° C. for 5 minutes to let the beads dry. Then the beads were resuspended in 30 µl resuspension bufferand incubated at room temperature for 5 minutes, placed on the magnetic stand for 5 minutes, and finally 50 µl supernatant was transferred to a new tube. One microliter was finally loaded on an Agilent Technologies 2100 bioanalyzer using a DNA 1000 assay to determine the quality of the purified digested DNA.

Cluster generation was performed according to the Illumina cBot User Guide (www DOT illumina.com, part #15006165 RevE). Briefly, 1 µl of a 10 nM TruSeq DNA library stock DNA was denatured with NaOH, diluted to 10 pM and hybridized onto the flowcell. The hybridized fragments are sequentially amplified, linearized and end-blocked according to the Illumina Paired-end Sequencing user guide protocol. After hybridization of the sequencing primer, sequencing-by-synthesis was performed using the HiSeq 2000 sequencer with a 101 cycle protocol according to the instructions of the manufacturer. The sequenced fragments were denaturated with NaOH using the HiSeq 2000 and the index-primer was hybridized onto the fragments. The index was sequenced with a 7-cycle protocol. The fragments are denaturated with NAOH, sequentially amplified, linearized and end-blocked. After hybridization of the sequencing primer, sequencing-by-synthesis of the third read was performed using the HiSeq 2000 sequencer with a 101-cycle protocol.

$_{HRHT}$iCIC$^2$ Sequence Mapping and Classification

The raw sequence reads were checked for the existence of the first restriction enzyme recognition sequence in the sequencing direction. The sequence after the first enzyme recognition site was removed. If the bases of the recognition site after the overhang were not unambiguously, the read was further trimmed by removing all the bases after the end of the overhang. Then these trimmed sequences were aligned using the Burrows-Wheeler Alignment (BWA) tool to the whole human genome NCBI36/hg18 assembly and to the mouse NCBI37/mm9 assembly. Therefore the following default parameter set was used (with the value of the parameter in [ ] brackets):

bwa aln [options] <prefix> <in.fq>
  n NUM max #diff (int) or missing prob under 0.02 err rate (float) [0.04]
  o INT maximum number or fraction of gap opens [1]
  e INT maximum number of gap extensions, −1 for disabling long gaps [−1]
  i INT do not put an indel within INT bp towards the ends [5]
  d INT maximum occurrences for extending a long deletion [10]
  l INT seed length [32]
  k INT maximum differences in the seed [2]
  m INT maximum entries in the queue [2000000]
  t INT number of threads [1]
  M INT mismatch penalty [3]
  O INT gap open penalty [11]
  E INT gap extension penalty [4]
  R INT stop searching when there are >INT equally best hits [30]
  q INT quality threshold for read trimming down to 35 bp [0]
  f FILE file to write output to instead of stdout
  B INT length of barcode
  L log-scaled gap penalty for long deletions
  N non-iterative mode: search for all n-difference hits (slooow)
  I the input is in the Illumina 1.3+ FASTQ-like format
  b the input read file is in the BAM format
  0 use single-end reads only (effective with −b)
  1 use the 1st read in a pair (effective with −b)
  2 use the 2nd read in a pair (effective with −b)
  Y filter Casava-filtered sequences In case of using a second restriction enzyme (and thus not in the case of sonication) the unique sequences were then aligned in a second step to a masked genome, excluding the sequence parts between second restriction enzymes and that did not contain a first enzyme recognition site. Finally, only those sequences were paired using the SAMtools to generate paired-end Binary Alignment/Map (BAM) files, which showed in both the whole and masked genome reference sequences a unique alignment. Note: the alignements are unique, but nevertheless contain mismatches etc., which are either do to sequencing errors or hint a difference of our cells/mice to the reference genome. Unfortunately, there is also no way of distinguishing false positive or false negative alignments. Consequently, the resulting paired-end sequences then contain the interaction information with an error rate determined by the error rate of sequencing, the quality of the reference sequence, and the difference the DNA sequence of our cells/mice to this reference genome. A rough estimate of the false positive and false negative results for unique sequences without mismatches at the end of this process using known error rates indicate the error to be smaller than 1% after accumulation of errors and the reduction of errors due to our procedure. This can be also deducted from the reduction of sequence pairs from the initial raw sequence throughout the entire process to the final result.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method for identifying nucleotide sequences which are involved in interactions of one or more nucleotide sequences from one or more regions of interest in a three-dimensional DNA structure with other nucleotides sequences in the three-dimensional DNA structure, comprising the steps of:
   (a) providing a sample comprising cross-linked DNA generated from cross-linked chromatin from a cell or tissue or nuclei sample;
   (b) forming cross-linked nucleotide sequences by digesting the cross-linked DNA with a first restriction enzyme;
   (c) producing ligated cross-linked nucleotide sequences by ligating an end of one nucleotide sequence of the cross-linked nucleotide sequences to an end of another nucleotide sequence of the cross-linked nucleotide sequences;
   (d) forming ligated molecules by reversing the cross-links of the ligated cross-linked nucleotide sequences;
   (e) forming fragmented molecules of the one or more nucleotide sequences from the one or more regions of interest by fragmenting the ligated molecules from step (d);
   (f) generating enriched fragments on a microarray or beads by hybridising the fragmented molecules of step (e) to one or more oligonucleotide probes that only specifically hybridize to the sequences in the three-dimensional DNA structure which are adjacent to the cleavage site of the first restriction enzyme in the regions of interest, wherein the one or more oligonucleotide probes are spotted on the microarray or captured on the beads, or by hybridising the fragmented molecules of step (e) to the one or more oligonucleotide probes present in a solution, and subsequently capturing complexes formed by the fragmented molecules of step (e) and the one or more oligonucleotide probes on the beads; and
   (g) identifying the nucleotide sequences which are involved in the interactions of the one or more nucleotide sequences from the one or more regions of interest in the three-dimensional DNA structure with the other nucleotides sequences in the three-dimensional DNA structure by analysing the nucleotide sequences of the enriched fragments.

2. The method according to claim 1, wherein the first restriction enzyme is a restriction enzyme that recognises a 6-8 bp recognition site.

3. The method according to claim 1, wherein in step (e) the ligated molecule is fragmented by digestion with a second restriction enzyme.

4. The method according to claim 3, wherein the second restriction enzyme recognises a 4 or 5 bp nucleotide sequence recognition site.

5. The method according to claim 1, wherein in step (e) the ligated molecule is fragmented using a combination of HpyCH21V, MspI, HinPII, and TaqI restriction enzymes or using a limited digestion by a general nuclease.

6. The method according to claim 1, wherein after step (e) and before step (f), the DNA ends of the fragmented molecules are repaired.

7. The method according to claim 1, wherein after step (e) and before step (f), an adapter is ligated to the ends of the fragmented molecules for sequencing purposes.

8. The method according to claim 7, wherein the adapter comprises an address sequence.

9. The method according to claim 1, wherein step (g) comprises high throughput sequencing of the enriched fragments.

10. The method according to claim 1, wherein the one or more regions of interest are 1-10 MB.

* * * * *